United States Patent [19]
Oh et al.

[11] Patent Number: 5,985,899
[45] Date of Patent: Nov. 16, 1999

[54] SELECTIVE THROMBIN INHIBITORS

[75] Inventors: Yeong Soo Oh; Sang Soo Kim; Sang Yeul Hwang; Mi Kyung Yun; Seong Ryul Hwang; Seong Won Hong; Yong Hee Lee; Yi Na Jeong; Koo Lee; You Seung Shin, all of Daejeon, Rep. of Korea

[73] Assignee: LG Chemical Ltd., Rep. of Korea

[21] Appl. No.: 08/967,661

[22] Filed: Nov. 10, 1997

Related U.S. Application Data

[62] Division of application No. 08/586,208, Jan. 16, 1996, Pat. No. 5,747,535.

[30]   Foreign Application Priority Data

Apr. 28, 1995  [KR]   Rep. of Korea ...................... 95-10383

[51] Int. Cl.$^6$ ....................... A61K 31/445; C07D 211/34
[52] U.S. Cl. ............................................. 514/330; 546/226
[58] Field of Search .............................. 546/226; 514/330

[56]   References Cited

U.S. PATENT DOCUMENTS

| | | | |
|---|---|---|---|
| 4,201,863 | 5/1980 | Okamoto et al. ...................... | 540/166 |
| 4,248,192 | 2/1981 | Okamoto et al. ...................... | 540/166 |
| 5,518,735 | 3/1996 | Sturzebecher et al. ................ | 424/449 |

FOREIGN PATENT DOCUMENTS

| | | |
|---|---|---|
| WO 94/18185 | 8/1994 | Germany . |
| WO 92/165549 | 10/1992 | WIPO . |

OTHER PUBLICATIONS

Kikumoto, R. et al., Selective Inhibition of Thrombin by (2R, 4R)–4–Methyl–1–[N$^2$–(3–methyl–1,2,3,4–tetrahydro–8–quinolinyl)sulfonyl]–L–arginyl)–2–piperidinecarboxylic Acid, Biochemistry 1984, vol. 23, pp. 85–90.

Banner, D., et al., Crystallographic Analysis at 3.0–A Resolution of the Binding of Human Thrombin of Four Active Site–directed Inhibitors*, The Journal of Biological Chemistry, 1991, vol. 266, No. 30, Oct. 25, pp. 20085–20093, 1991.

Hilpert, K. et al., Design and Synthesis of Potent and Highly Selective Thrombin Inhibitors, J. Med. Chem., 1994, 37, 3889–3901.

Lottenberg, R. et al., Assay of Coagulation Proteases Using Peptide Chromogenic and Fluorogenic Substrates, vol. 80, pp. 341–361, 1981.

Hofsteenge, J. et al., Enzymatic Properties of Proteolytic Derivatives of Human α–Thrombin, Biochemistry 1988, vol. 27, pp. 2144–2151.

Stuerzebecker et al., Chemical Abstract, vol. 123 (1995) 275199.

Stuerzebecker et al., Chemical Abstract, vol. 118 (1993) 7392.

Stuerzebecker et al., Chemical Abstract, vol. 107 (1987) 97532.

Wagner et al., Chemical Abstract, vol. 100 (1984) 210409.

Stuerzebecker et al., Chemical Abstract, vol. 99 (1983) 18600.

Stuerzebecker et al., Chemical Abstract, vol. 96 (1982) 173930.

Wagner et al., Chemical Abstract, vol. 96 (1982) 104709.

Stuerzebecker et al., Chemical Abstract, vol. 96 (1982) 48156.

Stuerzebecher et al., Chemical Abstracts, vol. 118, abstract 169610, 1993.

Primary Examiner—Richard L. Raymond
Attorney, Agent, or Firm—Hunton & Williams

[57]   ABSTRACT

The present invention relates to a novel selective thrombin inhibitor having the following formula (I), which is also effective by oral administration:

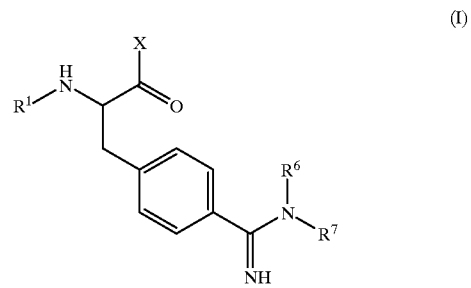

in which

R$^1$ represents acetyl substituted with aryl or aryloxy, or represents sulfonyl substituted with substituted or unsubstituted aryl or N-containing heterocyclic group, X represents a group of formula

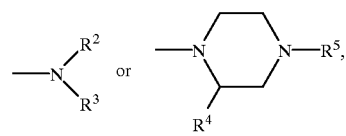

R$^2$ and R$^3$ independently of one another represent hydrogen; cycloalkyl substituted or unsubstituted with carboxyl or alkoxycarbonyl; arylalkyloxy; hydroxy; or lower alkyl substituted or unsubstituted with carboxyl, alkoxycarbonyl or hydroxy, or R$^2$ and R$^3$ together with nitrogen atom to which they are attached can form a piperidine group substituted with carboxyl or alkoxycarbonyl, R$^4$ represents hydrogen, lower alkyl or lower alkoxy, R$^5$ represents alkanesulfonyl; alkoxycarbonyl; alkylcarbonyl; formyl; lower alkyl; aryl substituted or unsubstituted with alkoxy or haloalkyl; or hydroxy-substituted lower alkyl, and R$^6$ and R$^7$ independently of one another represent hydrogen, lower alkyl or amino, and to a process for preparation thereof and a pharmaceutical composition for thrombin inhibition which comprises the compound of formula (I) as an active ingredient.

5 Claims, No Drawings

SELECTIVE THROMBIN INHIBITORS

This is a Divisional of U.S. patent application Ser. No. 08/586,208, filed Jan. 16, 1996, now U.S. Pat. No. 5,747,535.

BACKGROUND OF THE INVENTION

1. Field of the Invention

The present invention relates to a novel selective thrombin inhibitor having the following formula (I):

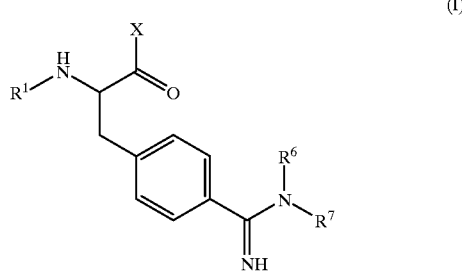

in which $R^1$ represents acetyl substituted with aryl or aryloxy, or represents sulfonyl substituted with substituted or unsubstituted aryl or N-containing heterocyclic group, X represents a group of formula

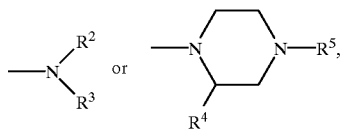

$R^2$ and $R^3$ independently of one another represent hydrogen; cycloalkyl substituted or unsubstituted with carboxyl or alkoxycarbonyl; arylalkyloxy; hydroxy; or lower alkyl substituted or unsubstituted with carboxyl, alkoxycarbonyl or hydroxy, or $R^2$ and $R^3$ together with nitrogen atom to which they are attached can form a piperidine group substituted with carboxyl or alkoxycarbonyl, $R^4$ represents hydrogen, lower alkyl or lower alkoxy, $R^5$ represents alkanesulfonyl; alkoxycarbonyl; alkylcarbonyl; formyl; lower alkyl; aryl substituted or unsubstituted with alkoxy or haloalkyl; or hydroxy-substituted lower alkyl, and $R^6$ and $R^7$ independently of one another represent hydrogen, lower alkyl or amino.

Some of the compounds of formula (I) can shows an effective thrombin inhibitory activity even through oral administration and therefore, is very valuable.

The present invention also relates to a process for preparing the compound of formula (I) and to a pharmaceutical composition for thrombin inhibition which comprises the compound of formula (I) as an active ingredient.

2. Background Art

It has been generally known that the process for blood coagulation involves numerous complicated enzyme reactions of which the final step includes a reaction of converting prothrombin into thrombin. Thrombin produced from the final step of blood coagulation process activates platelets and converts fibrinogen into fibrin which is then converted into a higher molecular substance by polymerization and cross-linked by the action of activated blood factor XIII to form insoluble blood clotting. Accordingly, thrombin plays an important role in blood coagulation process. Thrombin also activates blood factors V and VIII which in turn accelerates the blood coagulation by a feed-back mechanism.

Thus, since thrombin inhibitors act as effective anti-coagulants and, at the same time, can inhibit the platelet activation and the production and stabilization of fibrin, for a long time, many attempts have been made to find out a method for prevention of blood coagulation and for treatment of various thrombosis using a novel compound which can inhibit thrombin activity.

However, the compound capable of inhibiting only thrombin activity is restricted in use as the effective anti-coagulant and thrombolytic agent. The reason is that since thrombin is one of serine-proteases and numerous serine-proteases similar to trypsin, typically plasmin, are present in human body, particularly in blood, the effective thrombin inhibitor generally also has a high inhibitory activity against such serine-proteases. According to such characteristic feature of thrombin, in development of thrombin inhibitors it is very important that the inhibitor compound has a less inhibitory activity toward a prototype serine protease such as trypsin than thrombin.

Under such conditions, numerous studies have been conducted to develop a selective thrombin inhibitor which can effectively inhibit thrombin and, at the same time, has a little trypsin inhibitory activity. As a result, Argatroban having the following formula (A) as an arylsulfonylarginine-based compound has been developed (see, U.S. Pat. Nos. 4,258,192 and 4,201,863).

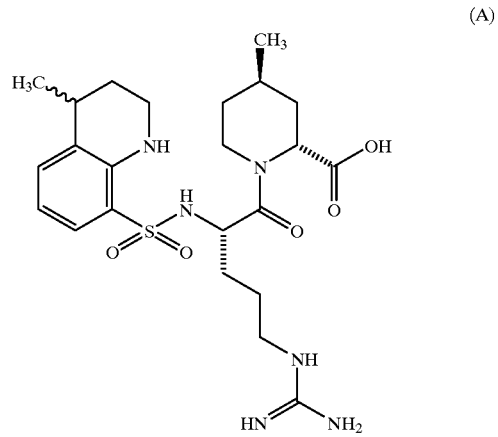

Argatroban shows a high inhibitory activity for thrombin which is 250 times as high as the activity for trypsin (see, Biochemistry 1984, 23, p85–90). However, it can be obtained only through a complicated synthetic procedure. It has been launched on market in Japan in 1990.

In addition, NAPAP having the following formula (B) as a benzamidine-based arylsulfonyl compound has also been developed.

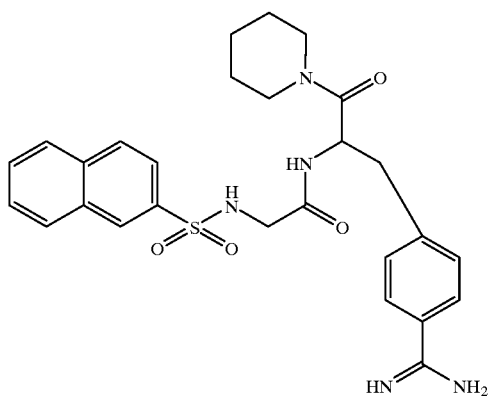

(B)

This compound can be readily synthesized and has an effective thrombin inhibitory activity. However, it has a disadvantage in that the thrombin inhibitory activity is merely 50 times as high as the activity for trypsin (see, J. Biol. Chem. 1991, 266, p20085–20093).

Further, Ro 46-6240 having the following formula (C) has been reported as the compound having an improved selectivity for thrombin over trypsin. This compound shows a possibility of development as an intravenous injectable formulation due to its short half-life in blood, but does not show any possibility for oral administration (see, J. Med. Chem. 1994, 37, 3889–3901).

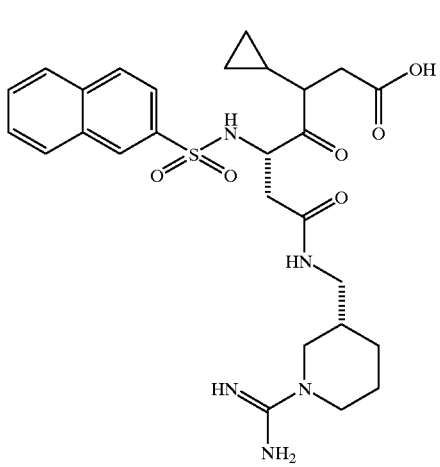

(C)

In addition, a piperazide-based compound as recently developed has been reported as having somewhat possibility for oral administration in rat but having a low selectivity for thrombin (see WO 94/18185). Thus, such compounds did not come up to the expectation in this art.

Therefore, the present inventors have extensively studied to develop a certain compound which can be easily synthesized, shows an effective thrombin inhibitory activity with a high selectivity for thrombin over trypsin and can also be administered via oral route. As a result, we have identified that the thrombin inhibitor of formula (I) according to the present invention can achieve such purpose and thus completed the present invention.

Accordingly, it is an object of the present invention to provide a novel thrombin inhibitor of formula (I), as defined above, which can be administered via oral route and has a high selectivity for thrombin.

It is another object of the present invention to provide a process for preparing the thrombin inhibitor of formula (I).

Further, it is still another object of the present invention to provide a pharmaceutical composition for prevention of blood coagulation and treatment of various thrombosis, which comprises the thrombin inhibitor of formula (I) as an active ingredient.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the disclosure of invention, in addition to the scope of the invention defined by the claims.

DISCLOSURE OF INVENTION

In one aspect, the present invention relates to a novel compound represented by the following formula (I):

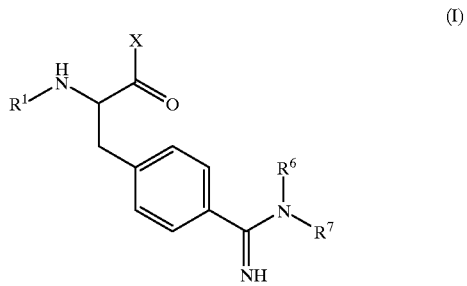

(I)

its pharmaceutically acceptable salt, hydrate, solvate and isomer, in which $R^1$ represents acetyl substituted with aryl or aryloxy, or represents sulfonyl substituted with substituted or unsubstituted aryl or N-containing heterocyclic group, X represents a group of formula

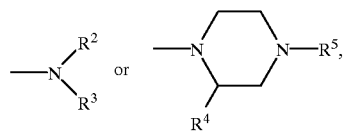

$R^2$ and $R^3$ independently of one another represent hydrogen; cycloalkyl substituted or unsubstituted with carboxyl or alkoxycarbonyl; arylalkyloxy; hydroxy; or lower alkyl substituted or unsubstituted with carboxyl, alkoxycarbonyl or hydroxy, or $R^2$ and $R^3$ together with nitrogen atom to which they are attached can form a piperidine group substituted with carboxyl or alkoxycarbonyl, $R^4$ represents hydrogen, lower alkyl or lower alkoxy, $R^5$ represents alkanesulfonyl; alkoxycarbonyl; alkylcarbonyl; formyl; lower alkyl; aryl substituted or unsubstituted with alkoxy or haloalkyl; or hydroxy-substituted lower alkyl, and $R^6$ and $R^7$ independently of one another represent hydrogen, lower alkyl or amino.

In the definition for each substituent of the compound of formula (I) according to the present invention, the term "lower alky" denotes a saturated, straight or branched hydrocarbon radical having 1 to 4 carbon atoms such as methyl, ethyl, isopropyl, isobutyl, t-butyl, etc.; the term "aralkyloxy" denotes an alkoxy group substituted with aromatic ring such as benzyloxy, etc.; and the term "cycloalkyl" denotes a cyclic alkyl group having 3 to 8 carbon atoms such as cyclopentyl.

Among the compound of formula (I) above, the preferred one is the compounds in which $R^1$ represents acetyl substituted with naphthyl or naphthyloxy, or represents sulfonyl substituted with naphthyl or phenyl which can be substituted or unsubstituted with one to four substituents selected from the group consisting of lower alkyl, lower alkoxy and dialkylamino, X represents a group of formula

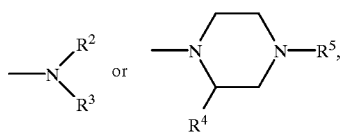

$R^2$ and $R^3$ independently of one another represent $C_{3-6}$ cycloalkyl substituted or unsubstituted with carboxyl or methoxycarbonyl; benzyloxy; lower alkyl substituted or unsubstituted with carboxyl, methoxycarbonyl or hydroxy; or hydroxy, or $R^2$ and $R^3$ together with nitrogen atom to which they are attached can form a piperidine group substituted with carboxyl or methoxycarbonyl, $R^4$ represents hydrogen, $R^5$ represents methanesulfonyl, ethoxycarbonyl, formyl, ethyl, phenyl, methylcarbonyl, hydroxyethyl, or phenyl which can be substituted or unsubstituted with trifluoromethyl or ethoxy, and $R^6$ and $R^7$ independently of one another represent hydrogen, methyl or amino.

Typical example of the compound of formula (I) according to the present invention includes the following:

(S)-N-cyclopentyl-N-methyl-3-(4-amidrazonophenyl)-2-(2-naphthylsulfonylamino)propionamide, (S)-N-butyl-N-methyl-3-(4-amidrazonophenyl)-2-(2-naphthylsulfonylamino)propionamide, (S)-N-cyclopentyl-N-propyl-3-(4-amidrazonophenyl)-2-(2-naphthylsulfonylamino)propionamide, (S)-N-cyclopentyl-N-(2-benzyloxyethyl)-3-(4-amidrazonophenyl)-2-(2-naphthylsulfonylamino)propionamide, (S)-N-cyclopentyl-N-butyl-3-(4-amidrazonophenyl)-2-(2-naphthylsulfonylamino)propionamide, (S)-N-cyclopentyl-N-ethyl-3-(4-amidrazonophenyl)-2-(2-naphthylsulfonylamino)propionamide, (S)-N-cyclopentyl-N-methyl-3-[4-(methylamidino)phenyl]-2-(2-naphthylsulfonylamino)propionamide, (S)-N-cyclopentyl-N-methyl-3-[4-(1,1-dimethylamidino)phenyl]-2-(2-naphthylsulfonylamino)propionamide, (S)-N-cyclopentyl-N-methyl-3-(4-amidrazonophenyl)-2-[(4-methoxy-2,3,6-trimethylbenzene)sulfonylamino]propionamide, (S)-N-cyclopentyl-N-hydroxy-3-(4-amidrazonophenyl)-2-(2-naphthylsulfonylamino)propionamide, (S)-N-cyclopentyl-N-(2-hydroxyethyl)-3-(4-amidrazonophenyl)-2-(2-naphthylsulfonylamino)propionamide, (S)-N-cyclopentyl-N-methyl-3-[4-(methylamidino)phenyl]-2-[(4-methoxy-2,3,6-trimethylbenzene)sulfonylamino]propionamide, (S) -N,N-dimethyl-3-(4-amidrazonophenyl)-2-(2-naphthylsulfonylamino)propionamide, (S)-N,N-dimethyl-3-[4-(1-methylamidino)phenyl]-2-(2-naphthylsulfonylamino)propionamide, (S)-N-cyclohexyl-N-methyl-3-(4-amidrazonophenyl)-2-(2-naphthylsulfonylamino)propionamide, (S)-N-cyclopropyl-N-methyl-3-(4-amidrazonophenyl)-2-(2-naphthylsulfonylamino)propionamide, (S)-3-[4-(amidrazono)-phenyl]-N-cyclopentyl-N-methyl-2-(2-naphthalen-1-yl-acetylamino)-propionamide, (S)-3-[4-(amidrazono)-phenyl]-N-cyclopentyl-N-methyl-2-(5-dimethylamino-naphthalene-1-sulfonylamino)-propionamide, (S)-3-[4-(amidrazono)-phenyl]-N-cyclopentyl-N-methyl-2-(5-methoxy-naphthalene-1-sulfonylamino)-propionamide, (S)-2-[4-(amidrazono)-phenyl]-N-cyclopentyl-N-methyl-2-(6,7 -dimethoxy-naphthalene-2-sulfonylamino)-propionamide, (S)-3-[4-(methylamidino)-phenyl]-N-cyclopentyl-N-methyl-2-(5-dimethylamino-naphthalene-1-sulfonylamino)-propionamide, (S)-3-[4-(amidrazono)-phenyl]-N-cyclopentyl-N-methyl-2-(naphthalene-1-sulfonylamino)-propionamide, (S)-3-[4-(amidrazono)-phenyl]-N-cyclopentyl-N-methyl-2-[2-(naphthalene-1-yl-oxy)acetylamino]-propionamide, (S)-3-[4-(amidrazono)-phenyl]-N-cyclopentyl-N-methyl-2-[2-(naphthalene-2-yl-oxy)acetylamino]-propionamide, {[3-(4-amidrazono-phenyl)-(S)-2-(naphthalene-2-sulfonylamino)-propionyl]-methylamino}-acetic acid methyl ester, {[3-(4-amidrazono-phenyl)-(S)-2-(naphthalene-2-sulfonylamino)-propionyl]-methylamino}-acetic acid, (S)-2-{[3-(4-amidrazono-phenyl)-(S)-2-(naphthalene-2-sulfonylamino)-propionyl]-methylamino}-propionic acid methyl ester, (S)-2-{[3-(4-amidrazono-phenyl)-(S)-2-(naphthalene-2-sulfonylamino)-propionyl]-methylamino}-propionic acid, (R)-2-{[3-(4-amidrazono-phenyl)-(S)-2-(naphthalene-2-sulfonylamino)-propionyl]-methylamino}-propionic acid methyl ester, (R)-2-{[3-(4-amidrazono-phenyl)-(S)-2-(naphthalene-2-sulfonylamino)-propionyl]-methylamino}-propionic acid, (R)-2-{[3-(4-amidrazono-phenyl)-(S)-2-(naphthalene-2-sulfonylamino)-propionyl]-methylamino}-3-methyl-butyric acid methyl ester, (R)-2-{[3-(4-amidrazono-phenyl)-(S)-2-(naphthalene-2-sulfonylamino)-propionyl]-methylamino}-3-methyl butyric acid, 3-{[3-(4-amidrazono-phenyl)-(S)-2-(naphthalene-2-sulfonylamino)-propionyl]-methylamino}-propionic acid methyl ester, 3-{[3-(4-amidrazono-phenyl)-(S)-2-(naphthalene-2-sulfonylamino)-propionyl]-methylamino}-propionic acid, 4-{[3-(4-amidrazono-phenyl)-(S)-2-(naphthalene-2-sulfonylamino)-propionyl]-methylamino}-butyric acid methyl ester, 4-{[3-(4-amidrazono-phenyl)-(S)-2-(naphthalene-2-sulfonylamino)-propionyl]-methylamino}-butyric acid, {[3-(4-amidrazono-phenyl)-(S)-2-(naphthalene-2-sulfonylamino)-propionyl]-cyclopropylamino}-acetic acid methyl ester, {[3-(4-amidrazono-phenyl)-(S)-2-(naphthalene-2-sulfonylamino)-propionyl]-cyclopropylamino}-acetic acid, {[3-(4-amidrazono-phenyl)-(S)-2-(naphthalene-2-sulfonylamino)-propionyl]-butylamino}-acetic acid methyl ester, {[3-(4-amidrazono-phenyl)-(S)-2-(naphthalene-2-sulfonylamino)-propionyl]-butylamino}-acetic acid, {[3-(4-amidrazono-phenyl)-(S)-2-(naphthalene-2-sulfonylamino)-propionyl]-cyclopentylamino}-acetic acid methyl ester, {[3-(4-amidrazono-phenyl)-(S)-2-(naphthalene-2-sulfonylamino)-propionyl]-cyclopentylamino}-acetic acid, 1-{[3-(4-amidrazono-phenyl)-(S)-2-(naphthalene-2-sulfonylamino)-propionyl]-methylamino}-cyclopentane carboxylic acid methyl ester, 1-{[3-(4-amidrazono-phenyl)-(S)-2-(naphthalene-2-sulfonylamino)-propionyl]-methylamino}-cyclopentane carboxylic acid, 2-{[3-(4-amidrazono-phenyl)-(S)-2-(naphthalene-2-sulfonylamino)-propionyl]-methylamino}-cyclopentane carboxylic acid ethyl ester, 2-{[3-(4-amidrazono-phenyl)-(S)-2-(naphthalene-2-sulfonylamino)-propionyl]-methylamino}-cyclopentane carboxylic acid, (S)-2-{[3-(4-amidrazono-phenyl)-(S)-2-(naphthalene-2-sulfonylamino)-propionyl]-methylamino}-3-methyl-butyric acid methyl ester, 1-[3-(4-amidrazono-phenyl)-(S)-2-(naphthalene-2-sulfonylamino)-propionyl]-piperidine-(R)-2-carboxylic acid methyl ester, 1-[3-(4-amidrazono-phenyl)-(S)-2-(naphthalene-2-sulfonylamino)-propionyl]-piperidine-(R)-2-carboxylic acid, (S)-naphthalene-2-sulfonic acid [1-(4-amidrazono)benzyl-2-(4-methylsulfonyl-piperazinyl)-2-oxoethyl]amide, (S)-naphthalene-2-sulfonic acid [1-(4-amidrazono)benzyl-2-oxo-2-(4-ethoxycarbonyl-piperazinyl)-ethyl]amide, (S)-naphthalene-2-sulfonic acid [1-(4-amidrazono)benzyl-2-(4-formyl-piperazinyl)-2-oxoethyl]amide, (S)-naphthalene-2-sulfonic acid [1-(4-amidrazono)benzyl-2-(4-ethyl-piperazinyl)-2-oxoethyl]amide, (S)-naphthalene-2-sulfonic acid [1-(4-amidrazono)benzyl-2-oxo-2-(4-phenyl-piperazinyl)-ethyl]amide, (S)-naphthalene-2-sulfonic acid [1-(4-amidrazono)benzyl-2-oxo-2-[4-(3-trifluoromethylphenyl)-piperazinyl)-ethyl]amide, (S)-naphthalene-2-sulfonic acid [2-(4-acetyl-piperazinyl)-1-(4-amidrazono)benzyl-2-oxoethyl]amide, (S)-naphthalene-2-sulfonic acid [1-(4-amidrazono)benzyl-2-oxo-2-[4-(2-hydroxyethyl)-piperazinyl]-ethyl]amide, and (S)-naphthalene-2-sulfonic acid [1-(4-amidrazono)benzyl-2-oxo-2-4- (2-ethoxyphenyl)-piperazinyl]-ethyl]amide.

The compound of formula (I) according to the present invention can also form a pharmaceutically acceptable salt. Suitable pharmaceutically acceptable salts for the compound (I) can include an acid addition salt formed with acids which can form a non-toxic acid addition salt containing pharmaceutically acceptable anion, for example, inorganic acids such as hydrochloric acid, sulfuric acid, nitric acid, phosphoric acid, hydrobromic acid, hydroiodic acid, etc., organic carbonic acids such as tartaric acid, formic acid, citric acid, acetic acid, trichloroacetic acid, gluconic acid, benzoic acid, lactic acid, fumaric acid, maleic acid, etc., sulfonic acids such as methanesulfonic acid, benzenesulfonic acid, p-toluenesulfonic acid, naphthalenesulfonic acid, etc., and the like acids.

In addition, since the compound of formula (I) according to the present invention can include an asymmetric carbon atom in its structure, it can be present in the form of racemate, diastereomeric mixture and individual diastereomer. All of such isomers are included within the scope of the present invention.

That is, the isomers of the compound of formula (I) may be represented as follows:

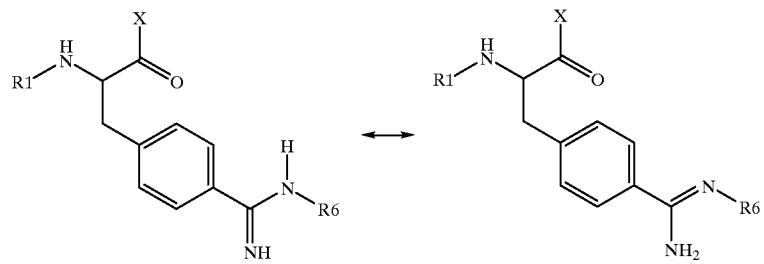

in which $R_6$ represents methyl or amino.

In another aspect, the present invention also relates to a process for preparing the compound of formula (I) as defined above.

According to the present invention, the compound of formula (I) can be prepared by reacting a compound of formula (II) with a compound of formula (III) as depicted in the following reaction scheme 1.

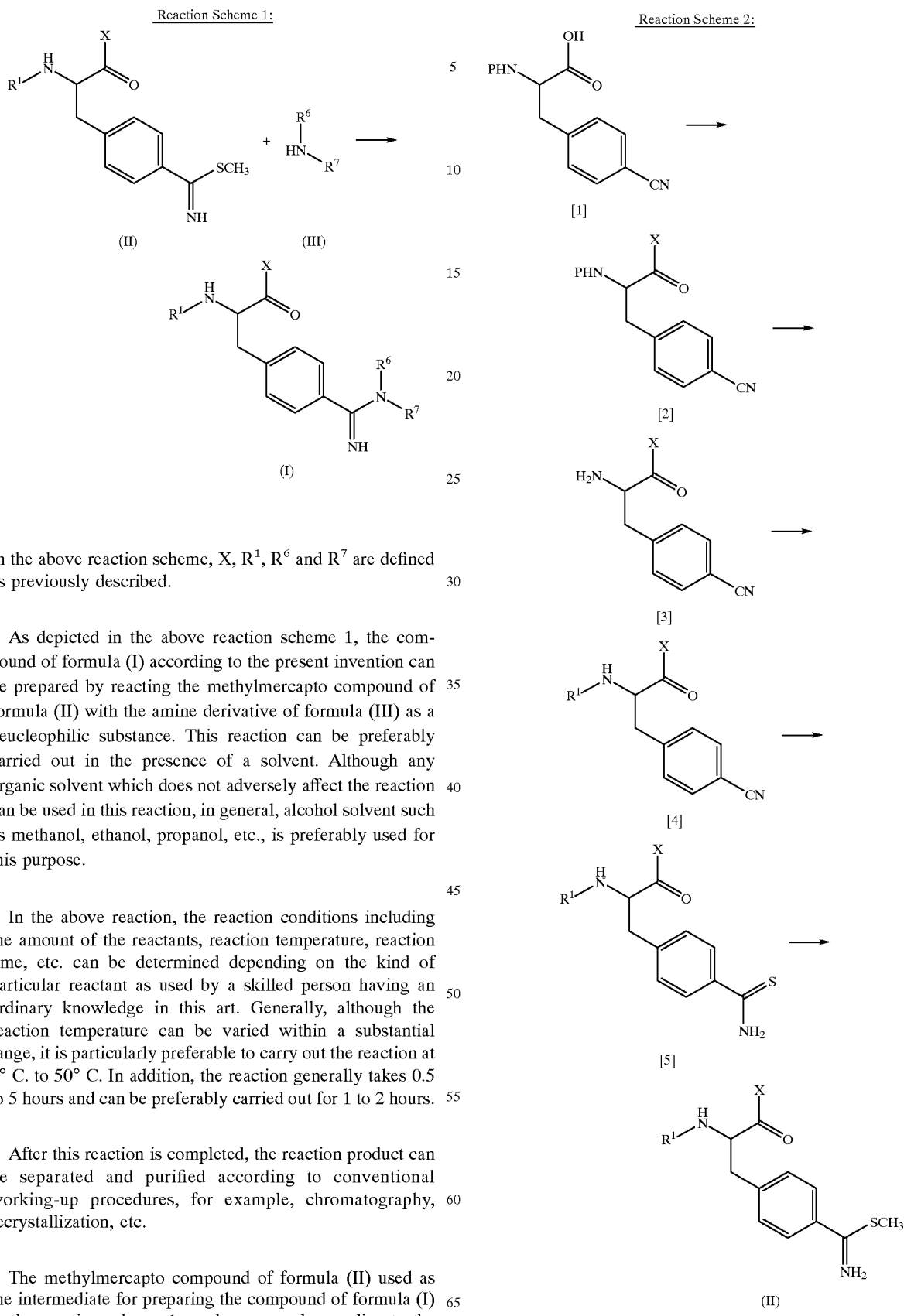

In the above reaction scheme, X, $R^1$, $R^6$ and $R^7$ are defined as previously described.

As depicted in the above reaction scheme 1, the compound of formula (I) according to the present invention can be prepared by reacting the methylmercapto compound of formula (II) with the amine derivative of formula (III) as a neucleophilic substance. This reaction can be preferably carried out in the presence of a solvent. Although any organic solvent which does not adversely affect the reaction can be used in this reaction, in general, alcohol solvent such as methanol, ethanol, propanol, etc., is preferably used for this purpose.

In the above reaction, the reaction conditions including the amount of the reactants, reaction temperature, reaction time, etc. can be determined depending on the kind of particular reactant as used by a skilled person having an ordinary knowledge in this art. Generally, although the reaction temperature can be varied within a substantial range, it is particularly preferable to carry out the reaction at 0° C. to 50° C. In addition, the reaction generally takes 0.5 to 5 hours and can be preferably carried out for 1 to 2 hours.

After this reaction is completed, the reaction product can be separated and purified according to conventional working-up procedures, for example, chromatography, recrystallization, etc.

The methylmercapto compound of formula (II) used as the intermediate for preparing the compound of formula (I) in the reaction scheme 1 can be prepared according to the reaction scheme 2 or 3 as depicted below.

Reaction Scheme 3:

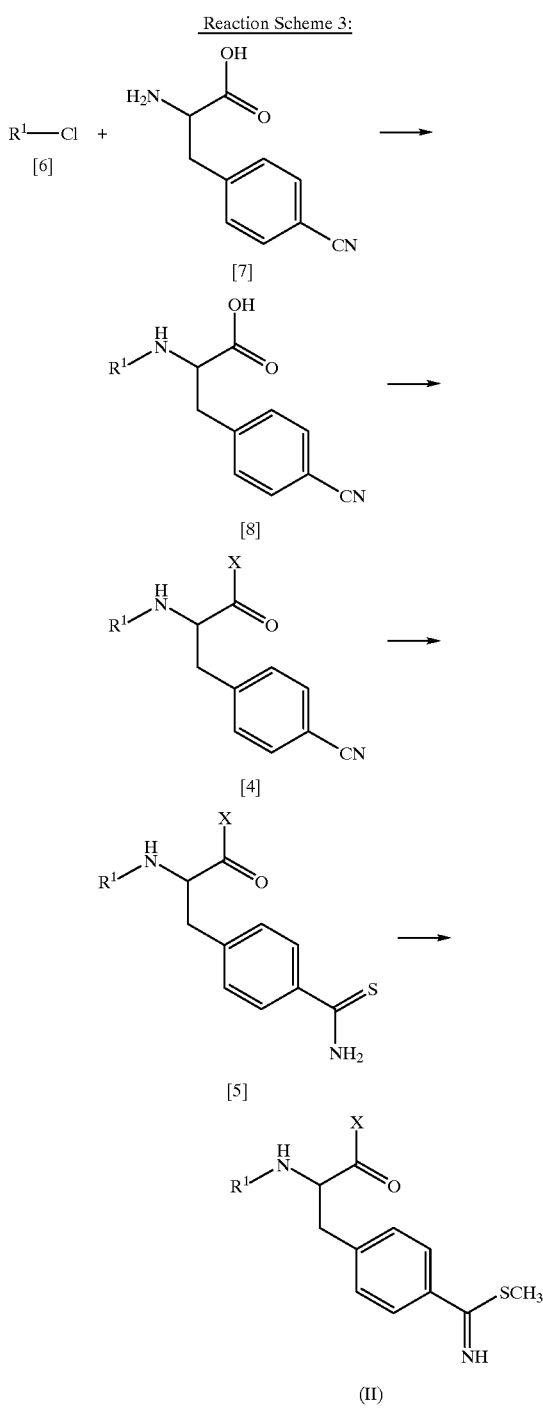

In the above reaction schemes,

X, $R^1$, $R^6$ and $R^7$ are defined as previously described, and P represents an amino-protecting group.

Hereinafter, the reaction schemes 2 and 3 are specifically explained.

In the reaction scheme 2, first the C-terminal of the compound [1] is coupled with the amine group X to prepare the compound [2] from which the amino-protecting group at N-terminal is removed to prepare the compound [3]. Then, the group $R^1$ is introduced into the deprotected N-terminal of the compound [3] to prepare the compound [4]. Alternatively, according to the reaction scheme 3, first the group $R^1$ is introduced into the N-terminal of the compound [7] and then the C-terminal is coupled with the amine group X to prepare the compound [4].

Specifically, according to the reaction scheme 2, the compound of formula [1] is coupled with the amine compound corresponding to the substituent X to obtain the compound of formula [2] from which the amino-protecting group at the N-terminal is removed to obtain the compound of formula [3]. Then, the group $R^1$ is introduced into the N-terminal of the compound [3] to produce the nitrile compound of formula [4] which is then saturated with hydrogen sulfide in the presence of pyridine and triethylamine to produce the thioamide compound of formula [5]. This thioamide compound is then methylated with a methylating agent such as iodomethane, dimethylsulfate, methyltriflate, etc., to obtain the desired methylmercapto compound of formula (II).

According to the reaction scheme 3, first the group $R^1$ is introduced into the N-terminal of the compound of formula [7] by reacting the compound [7] with the compound of formula [6] and then the amine group is introduced into the C-terminal of the resulting compound of formula [8] by coupling the compound [8] with the amine compound corresponding to the substituent X to obtain the compound of formula [4] which is then subjected to the same procedure as in the reaction scheme 2 to produce the desired methylmercapto compound of formula (II).

The coupling agent which can be used for the coupling procedure in the reaction schemes 2 and 3 includes one or more substances selected from the group consisting of dicyclohexylcarbodiimide (DCC), 3-ethyl-3'-(dimethylamino)propylcarbodiimide (EDC), bis-(2-oxo-3-oxazolidinyl)phosphinic acid chloride (BOP-Cl) and diphenylphosphorylazide (DPPA) but is not limited thereto.

Although the carboxylic acid compounds [1] and [7] used in the reaction schemes 2 and 3 can be used in their free acid forms, they can be preferably used in the form of their reactive derivatives, for example, an acid halide derivative or other activated ester derivative to facilitate the reaction. Particularly, the activated ester derivative of carboxylic acid is necessary for a coupling reaction with an amine compound to form an amide linkage or a coupling reaction with an alcohol to form an ester linkage. Such reactive derivatives include conventional derivatives which can be prepared according to the method conventionally used in this technical field. For example, as the acid halide derivative an acid chloride is included; and the activated ester derivative includes a carboxylic acid anhydride derived from alkoxycarbonyl halide such as methoxycarbonylchloride, isobutyloxycarbonylchloride, etc., and a coupling agent, N-hydroxyphthalimide-derived ester, N-hydroxysuccinimide-derived ester, N-hydroxy-5-norbonene-2',3'-dicarboxyimide-derived ester, 2,4,5-trichlorophenol-derived ester, etc., but is not limited thereto.

The thrombin inhibitory effect of the compound of formula (I) according to the present invention can be identified by determination of a dissociation constant Ki represented by the following equation according to the known method described in literature (see, Methods in enzymology V. 80, p341–361; Biochemistry 27, p2144–2151 (1988)].

$$Ki = \frac{[E]^* \cdot [I]^{}}{[EI]^{*}}$$

* [E] : concentration of the free enzyme
** [I] : concentration of the unbound inhibitor
*** [EI] : concentration of the enzyme-inhibitorcomplex The dissociation constant Ki denotes the degree of dissociation of the enzyme-thrombin inhibitor complex. Accordingly, the low dissociation constant means the high binding property of thrombin inhibitor to enzyme and therefore, is estimated that the thrombin inhibitor has a high inhibitory activity for thrombin. Such dissociation constant can be determined by reacting thrombin with a certain substrate which develops a color when it is hydrolyzed by the action of thrombin, and then measuring the degree of color development as a function of time by means of spectrophotometry.

In the present invention, Chromozym TH (Gly-Pro-Arg-4-nitroanilide acetate) is used as the substrate substance for thrombin, which develops the color by the action of thrombin. Chromozym TH is hydrolyzed by thrombin to produce yellow para-nitroaniline. Accordingly, the amount of yellow para-nitroaniline thus produced can be measured as the change of absorbance in the course of time to determine the thrombin inhibitory activity of the compound according to the present invention. That is, the enzyme activity can be determined from the rate of change in absorbance and then can be directly connected with the ability of the thrombin inhibitor to inhibit the enzyme activity (see, Methods in Enzymology, V. 80, p341–361, Biochemistry 27, p2144–2151, 1988).

To identify the selectivity for thrombin over trypsin of the compound of the present invention, the inhibitory activity for trypsin of the compound of formula (I) is measured as Ki value according to the same method as the above method for determination of thrombin inhibitory activity, and then the ratio of the activity for trypsin to the activity for thrombin is calculated. In this case, the procedure for determination of inhibitory activity for trypsin is substantially identical to that for thrombin, except that N-benzoyl-Val-Gly-Arg para-nitroanilide hydrochloride is used as the substrate.

As the result of determination of inhibitory activity for thrombin and trypsin of the compound of formula (I) according to the present invention, it can be identified that the compound of the present invention shows an excellent thrombin inhibitory activity and further has a high selectivity for thrombin against trypsin. Particularly, the selectivities of compounds of Examples 1 and 7 for thrombin against trypsin are approximately 2900 times and 26304 times, respectively, whereas the selectivities of the known thrombin inhibitors, argatroban (A) and NAPAP (B), are merely 250 times and 50 times, respectively. Accordingly, it can be seen that the compound (I) of the present invention achieves a significant improvement in the selectivity for thrombin against trypsin.

As mentioned above, since the novel compound of formula (I) according to the present invention is a thrombin inhibitor which shows a potent thrombin inhibitory activity even through oral administration and also has a high selectivity for thrombin over trypsin, it is useful for prophylaxis of blood coagulation and treatment of various thrombosis.

Accordingly, it is the third object of the present invention to provide a pharmaceutical composition for prophylaxis of blood coagulation and treatment of thrombosis which comprises the compound of formula (I) or its pharmaceutically acceptable salt as an active ingredient.

When the compound of formula (I) according to the present invention is administered to the subject host for clinical purpose, a daily dosage of the compound (I) can be varied preferably in the range of 0.001 mg to 10 mg per kg of body weight. However, if required for a certain patient, a specific dosage beyond the above mentioned dosage range can be determined depending on the a specific compound to be used, weight, sex and healthy condition of the respective patient, diet, administration time and method, secretion rate of the compound, other active component to be combined and severity of the diseases to be treated.

The compound of the present invention can be administered in the form of an injectable preparation or an oral preparation according to the desired purpose.

The injectable preparation, for example, sterilized, injectable aqueous or oily suspensions can be formulated using a suitable dispersing agent, wetting agent or suspending agent according to the known method conventionally used in the field of preparation of injections. As the aqueous solvent suitable for this purpose, water, Ringer's solution or isotonic NaCl solution can be used. In addition, although a sterilized fixing oil can be used as the solvent or suspending medium, any non-irritable fixing oil including mono- or di-glycerides can be used for the same purpose. Furthermore, a fatty acid such as oleic acid may be added to the injectable preparation.

The solid preparation for oral administration can be in the form of capsules, tablets, pills, powders and granules, with the capsule or tablet formulation being particularly useful. The tablets and pills can be prepared preferably in the enteric-coated formulation. In formulating the solid preparation, the active compound of formula (I) according to the present invention can be combined with a pharmaceutically acceptable carrier, for example, one or more inert diluent(s) such as sucrose, lactose, starch, etc., lubricants such as magnesium silicate, disintegrants, binders and the like.

One of the major characteristic features of the compound of formula (I) according to the present invention is that the compound of formula (I) exhibits a good pharmacological effect even when it is formulated in the form of an oral preparation and then administered via oral route. This can be demonstrated from the result of pharmacokinetic experiments in rat and dog as the experimental animal. That is, in such experiments it could be identified that the active compound of the present invention is retained in blood for a prolonged period when it is administered via oral route. Accordingly, the compound of formula (I) according to the present invention is more useful in view of the fact that it can be effectively used in the form of oral preparation.

Further, from the pharmacokinetic experiments it could also be identified that the active compound of the present invention can achieve the desired purpose without acute toxicity in mammals including rat and dog.

When the thrombin inhibitor according to the present invention is administered to obtain anti-coagulant and thrombolytic effects, it can be administered in combination with one or more substance(s) selected from the group consisting of thrombolytic agents and agents for inhibition of thrombocyte activity. As the thrombolytic agent which can be used for this purpose, t-PA, urokinase, streptokinase, etc. can be mentioned; and aspirin, ticlopidin, clopidrogel, 7E3 monoclonal antibody, etc. can be used as the agent for inhibition of thrombocyte activity.

However, it should be understood that the preparation containing the active compound of the present invention for treatment and prophylaxis of thrombosis is not limited to those described above and can include any preparation useful for the same purpose.

Hereinafter, the present invention will be more specifically explained by the working examples. However, it should be understood that the examples are given only for the explanation of the present invention and not intended to limit the present invention in any manner.

PREPARATION 1

Synthesis of Cyclopentyl-methylamine

To a solution of cyclopentanone (10 ml, 113 mmol) in methanol (50 ml) and water (50 ml) were added methylamine hydrochloride (7.6 g, 113 mmol) and sodium cyanoborohydride ($NaBH_3CN$) (7.1 g, 113 mmol). The mixture was heated to reflux for 12 hrs at pH 6. Methanol was evaporated under reduced pressure and the residue was cooled to 0° C., adjusted to pH 2 using 3N hydrochloric acid and then washed three times with diethyl ether. The aqueous layer was cooled again to 0° C. and then adjusted to pH 11 using 6N sodium hydroxide solution. To this mixture was added t-butyloxycarbonyl anhydride (24.5 g, 113 mmol) in dioxane (50 ml). The solution was stirred for 3 hours at room temperature and concentrated under reduced pressure to about 30 ml. The residue was extracted with ethyl acetate and washed with aqueous 0.5N hydrochloric acid and saturated sodium bicarbonate solutions. The organic layer was dried over anhydrous magnesium sulfate, filtered and concentrated under reduced pressure to obtain the white solid which was then purified by column chromatography (eluent=ethyl acetate:hexane=7:3 (v/v)). Upon purification, the obtained solid product was dissolved in 4N HCl-dioxane solution (60 ml) and the resulting solution was stirred for 30 minutes at room temperature. The solvent was evaporated in vacuo to obtain the title compound (13.7 g Yield: 90.5%).

$^1$H NMR($CD_3OD$, ppm) δ: 3.50(m, 1H), 2.68(s, 3H), 2.10(m, 2H), 1.86–1.50(m, 6H)

PREPARATION 2

Synthesis of (S)-N-cyclopentyl-N-methyl-3-(4-cyanophenyl-2-(butyloxtcarbonylamino) propionamide To a solution of (S)-3-(4-cyanophenyl)-2-(butyloxycarbonylamino)propionic acid (0.7 g, 2.41 mmole) in dimethylformamide (DMF, 6 ml) were added, 1-(3-dimethylaminopropyl)-3-ethylcarbodiimide hydrochloride (EDC, 0.7 g) and 1-hydroxybenzotriazole hydrate (HOBT, 0.4 g) at 0° C. The mixture was stirred until they are completely dissolved therein. To this reaction mixture were added the compound (0.4 g, 2.96 mmole) prepared in Preparation 1 and N-methylmorpholine (1.0 ml) and then the reaction temperature was slowly elevated to room temperature. The reaction solution was stirred for 3.5 hours. After the reaction is completed, the reaction solution was concentrated under reduced pressure to remove the volatile substances and the remaining residue was diluted with ethyl acetate, washed successively with aqueous saturated sodium hydrogen Carbonate solution, dilute hydrochloric acid and brine, dried over anhydrous sodium sulfate, filtered and then concentrated. The residue was purified by column chromatography (ethyl acetate:hexane=7:3 (v/v)) to obtain the purified title compound (0.65 g, Yield: 73.0%).

$^1$H NMR($CDCl_3$, ppm) δ: 7.61(m, 2H), 7.32(m, 2H), 5.48, 5.01–4.86, 4.12(3m, 3H), 2.75, 2.62(2s, 3H), 2.90–1.20(m, 17H)

Mass(FAB, m/e): 372($M^+$+1)

PREPARATION 3

Synthesis of (S)-N-cyclopentyl-N-methyl-3-(4-cyanophenyl)-2-(2-naphthylsulfonylamino) propionamide The compound (0.65 g, 1.75 mmole) prepared in Preparation 2 was dissolved in dichloromethane (3 ml) and then cooled to −10° C., and trifluoroacetic acid (TFA, 1 ml) was added thereto. The reaction mixture was stirred for 5 minutes, slowly warmed to room temperature, stirred for 30 minutes and then concentrated under reduced pressure to remove the volatile substances. The residue was dried by means of a vaccum pump and then 6 ml of DMF was added thereto. The mixture was cooled to 0° C. and of N,N-diisopropylethylamine (1 ml) was added thereto. The reaction mixture was warmed to room temperature and stirred for about 5 minutes. After addition of 2-naphthalenesulfonyl chloride (0.47 g, 2.07 mmole), the reaction mixture was stirred for one hour to complete the reaction and then concentrated under reduced pressure to remove the volatile substances. The residue was diluted with ethyl acetate, washed with saturated sodium hydrogen carbonated solution and brine, dried over anhydrous magnesium sulfate, filtered and concentrated. The residue was purified by column chromatography (ethyl acetate:hexane=1:1 (v/v)) to obtain the title compound (0.65 g, Yield: 80.2%).

$^1$H NMR($CDCl_3$, ppm) δ: 8.28(m, 1H), 7.87(m, 3H), 7.73(m, 3H), 7.49(m, 2H), 5.92(m, 1H), 4.50, 4.32, 3.76(m, m, m, 2H), 2.95(m, 2H), 2.36, 2.22(s, s, 3H), 1.60–1.20(m, 6H), 0.98, 0.80, 0.47(m, m, m, 2H)

Mass(FAB, m/e): 462($M^+$+1)

EXAMPLE 1

Synthesis of (S)-N-cyclopentyl-N-methyl-3-(4-amidrazonophenyl)-2-(2-naphthylsulfonylamino) propiionamide The compound (0.65 g, 1.41 mmole) prepared in Preparation 3 was dissolved in of pyridine (10 ml) and the resulting solution was introduced into a branched flask, to which triethylamine (0.45 ml) was added. The reaction flask was equipped so that hydrogen sulfide ($H_2S$) gas can be slowly introduced through one branch of the flask and discharged through another branch. The reaction solution was saturated with hydrogen sulfide gas, while stirring for about 10 minutes, during which the colorless solution was changed into green color and then gradually into dark brown. The flask was closed with rubber stopper and allowed to stand for 3 days at room temperature to complete the reaction. Then, the reaction solution was distilled under reduced pressure to remove the volatile substances and dried by means of a vaccum pump. To the obtained yellow solid were added acetone (15 ml) and iodomethane ($CH_3I$, 0.65 ml) together and this mixture was heated to reflux for 30 minutes. This reaction mixture was distilled again under reduced pressure to remove the volatile substances and dried by means of a vaccum pump. The residue was dissolved in absolute methanol (8 ml) and then stirred. To this mixture was added portionwise 80% hydrazine hydrate ($H_2NNH_2.H_2O$, 0.12 ml, 1.98 mmole) over three times at an interval of 10 minutes. After the reaction is completed, the reaction solution was concentrated and then purified by HPLC to obtain the title compound (0.63 g, Yield: 73.0%).

HPLC condition:

eluent=methanol water (75:25 v/v), each of which contains $CF_3COOH$ in the concentration of 0.1% wavelength=215 nm elution rate=20 ml/min.

column=Delta PAK $C_{18}$ 100 Å (30×300 mm)

$^1$H NMR(CD$_3$OD, ppm) δ: 8.28(d, 1H), 7.92(m, 3H), 7.70–7.50(m, 5H), 7.35(dd, 2H), 4.60, 4.45(t, t, 1H), 4.12, 3.99(m, m, 1H), 3.00, 2.87(m, m, 2H), 2.49, 2.26(s, s, 3H), 1.60–1.00, 0.73–0.52(m, m, 8H)

Mass(FAB, m/e): 494($M^+$+1)

PREPARATION 4

Synthesis of Butyl-methylamine Trifluoroacetic Acid Salt

N-butyloxycarbonylbutylamine (140 mg, 0.80 mmole) was dissolved in DMF (8 ml), and sodium hydride (NaH, 20 mg, 1 eq. wt.) and iodomethane (0.10 ml, 2 eq. wt.) were added thereto. The reaction mixture was stirred for 30 minutes at room temperature and filtered through celite bed and then concentrated under reduced pressure to remove the solvent. The residue was diluted with ethyl acetate, washed with 0.5N aqueous hydrochloric acid solution, dried over anhydrous magnesium sulfate and filtered. The organic layer was concentrated under reduced pressure and dried by means of a vaccum pump to obtain a white solid, which was then dissolved in dichloromethane and cooled down to 0° C. To this mixture was added 1 ml of trifluoroacetic acid (TFA). The reaction solution was stirred for 30 minutes at room temperature, concentrated under reduced pressure and then dried by means of a vaccum pump to obtain the title compound (0.16 g) in a quantitative yield.

$^1$H NMR(CDCl$_3$, ppm) δ: 1.02(t, 3H), 1.30–1.80(m, 4H), 3.04(s, 3H), 3.52(t, 2H), 8.20(s, 2H)

EXAMPLE 2

Synthesis of (S)-N-butyl-N-methyl-3-(4-amidrazonophenyl)-2-(2-naphthylsulfonylamino)propionamide The compound prepared in Preparation 4 was reacted according to the same procedure as Preparations 2 and 3 to obtain the intermediate (S)-N-butyl-N-methyl-3-(4-cyanophenyl)-2-(2-naphthylsulfonylamino) propionamide (0.23 g) which was used as the starting material. This starting material was treated according to the same procedure as Example 1 to obtain the purified title compound (0.1 g, Yield: 40.0%).

$^1$H NMR(CD$_3$OD, ppm) δ: 8.30(d, 1H), 7.98(m, 3H), 7.81–7.30(m, 7H), 4.50(m, 1H), 3.25–2.55(m, 4H), 2.78, 2.45(2s, 3H), 1.40–0.50(m, 7H)

Mass(FAB, m/e): 482($M^+$+1)

EXAMPLE 3

Synthesis of (S)-N-cyclopentyl-N-propyl-3-(4-amidrazonophenyl)-2-(2-naphthylsulfonylamino)propionamide The same procedure as Preparation 1, except that propylamine was used instead of methylamine, was carried out to obtain cyclopentyl-propylamine hydrochloride which was then treated according to the same procedure as Preparations 2 and 3 to obtain the intermediate (S)-N-cyclopentyl-N-propyl-3-(4-cyanophenyl)-2-(2-naphthylsulfonylamino)propionamide (0.15 g). This intermediate compound was used as the starting material and treated according to the same procedure as Example 1 to obtain the purified title compound (0.089 g, Yield: 55.1%).

$^1$H NMR(CD$_3$OD, ppm) δ: 8.35–7.35(m, 1H), 4.62–4.32 (m, m, 1H), 3.90, 3.70(m, m, 1H), 3.10–2.50(m, 4H), 1.70–0.50(m, 13H)

Mass(FAB, m/e): 522($M^+$+1)

EXAMPLE 4

Synthesis of (S)-N-cyclopentyl-N-(2-benzyloxyethyl)-3-(4-amidrazonophenyl)-2-(2-naphthylsulfonylamino)propionamide The same procedure as Preparation 1, except that 2-benzyloxyethylamine was used instead of methylamine, was carried out to obtain cyclopentyl- (2-benzyloxyethyl) amine hydrochloride which was then treated according to the same procedure as Preparations 2 and 3 to obtain the intermediate (S)-N-cyclo-pentyl-N-( 2-benzyloxyethyl)-3-(4-cyanophenyl)-2-(2-naphthylsulfonylamino) propionamide (0.15 g). This intermediate compound was used as the starting material and treated according to the same procedure as Example 1 to obtain the purified title compound (0.15 g, Yield: 93.8%).

$^1$H NMR(CD$_3$OD, ppm) δ: 8.30–7.15(m, 16H), 4.64(m, 1H), 4.48, 4.39(s, s, 1H), 4.14, 4.00, 3.75, 3.45 (m, m, m, m, 3H), 3.10–2.70(m, 5H), 1.62–1.00(m, 8H)

Mass(FAB, m/e): 614($M^+$+1)

EXAMPLE 5

Synthesis of (S)-N-cyclopentyl-N-butyl-3-(4-amidrazonophenyl)-2-(2-naphthylsulfonylamino)propionamide The same procedure as Preparation 1, except that butylamine was used instead of methylamine, was carried out to obtain butylcyclopentylamine hydrochloride which was then treated according to the same procedure as Preparations 2 and 3 to obtain the intermediate (S)-N-cyclopentyl-N-butyl-3-(4-cyanophenyl)-2-(2-naphthylsulfonylamino) propionamide (0.28 g). This intermediate compound was used as the starting material and treated according to the same procedure as Example 1 to obtain the purified title compound (0.18 g, Yield: 60%).

$^1$H NMR(CD$_3$OD, ppm) δ: 8.32(d, 1H), 7.96(m, 3H), 7.78–7.55(m, 5H), 7.42(dd, 2H), 4.62, 4.30(m, m, 1H), 4.02, 3.90(m, m, 1H), 3.10–2.75, 2.55(m, m, 4H), 1.65–0.80(m, 12H), 0.65 (t, 3H)

Mass(FAB, m/e): 536($M^+$+1)

EXAMPLE 6

Synthesis of (S)-N-cyclopentyl-N-ethyl-3-(4-amidrazonophenyl)-2-(2-naphthylsulfonylamino)propionamide The same procedure as Preparation 1, except that ethylamine was used instead of methylamine, was carried out to obtain cyclopentyl-ethylamine hydrochloride which was then treated according to the same procedure as Preparations 2 and 3 to obtain the intermediate (S)-N-cyclopentyl-N-ethyl-3-(4-cyanophenyl)-2-(2-naphthylsulfonylamino) propionamide (0.21 g). This intermediate compound was used as the starting material and treated according to the same procedure as Example 1 to obtain the purified title compound (0.11 g, Yield: 50.0%).

$^1$H NMR(CD$_3$OD, ppm) δ: 8.32(d, 1H), 7.97(m, 3H), 7.75–7.55(m, 5H), 7.42(m, 2H), 4.60, 4.38(m, m, 1H), 3.98, 3.87(m, m, 1H), 3.20–2.70(m, 4H), 1.65–1.00(m, 8H), 0.95, 0.58(t, t, 3H)

Mass(FAB, m/e): 508(M$^+$+1)

EXAMPLE 7

Synthesis of (S)-N-cyclopentyl-N-methyl-3-[4-(methylamidino)phenyl]-2-(2-naphthylsulfonylamino)propionamide The intermediate compound prepared in Preparation 3 was used as the starting material and treated according to the same procedure as Example 1, except that methylamine, instead of hydrazine, was added over 3 times at an interval of one hour, to obtain the purified title compound (0.064 g, Yield: 8%).

$^1$H NMR(CD$_3$OD, ppm) δ: 0.50–1.60(m, 8H), 2.00–2.49 (2s, 3H), 2.84(m, 1H), 2.96(m, 1H), 3.00(s, 3H), 4.05(m, 1H), 4.50(m, 1H), 7.20–8.30(m, 11H)

Mass(FAB, m/e): 493(M$^+$+1)

EXAMPLE 8

Synthesis of (S)-N-cyclopentyl-N-methyl-3-[4-(1,1-dimethylamidino)phenyl]-2-(2-naphthylsulfonylamino)propionamide The intermediate compound prepared in Preparation 3 was used as the starting material and treated according to the same procedure as Example 1, except that dimethylamine, instead of hydrazine, was added over three times at an interval of one hour, to obtain the purified title compound (0.18 g, Yield: 22%).

$^1$H NMR(CD$_3$OD, ppm) δ: 0.60–1.60(m, 8H), 2.29, 2.54 (2s, 3H), 2.95(m, 1H), 3.06(m, 1H), 3.09(s, 3H), 3.31(s, 3H), 4.16(m, 1H), 4.60(m, 1H), 7.20–8.30(m, 11H)

Mass(FAB, m/e): 507(M$^+$+1)

EXAMPLE 9

Synthesis of (S)-N-cyclopentyl-N-methyl-3-(4-amidrazonophenyl)-2 -(4-methoxy-2,3,6-trimethylbenzenesulfonylamino)propionamide The compound prepared in Preparation 2 was treated according to the same procedure as Preparation 3, except that 4-methoxy-2,3,6-trimethylbenzenesulfonyl chloride was used instead of 2-naphthalenesulfonyl chloride, to obtain the intermediate (S)-N-cyclopentyl-N-methyl-3-(4-cyanophenyl)-2-(4-methoxy-2,3,6-trimethylbenzenesulfonylamino)propionamide (0.27 g). This intermediate compound was used as the starting material and treated according to the same procedure as Example 1 to obtain the purified title compound (0.16 g, Yield: 57.1%).

$^1$H NMR(CD$_3$OD, ppm) δ: 7.62(d, 2H), 7.40(dd, 2H), 6.70(d, 1H), 4.35, 3.90(m, m, 2H), 3.83(d, 3H), 3.00 (m, 2H), 2.50(m, 9H), 2.1(s, 3H), 1.75–0.90(m, 8H)

Mass(FAB, m/e): 516(M$^+$+1)

PREPARATION 5

Synthesis of Cyclopentyl-hydroxylamine

Hydroxylamine hydrochloride (H$_2$NOH.HCl, 5.0 g, 71.95 mmole) was dissolved in water (14 ml), and methanol (30 ml) and cyclopentanone (5.1 ml, 57.66 mmole) were added thereto. The mixture was stirred, cooled to 0° C. and then adjusted to pH 8 by adding 6N aqueous sodium hydroxide solution. Sodium cyanoborohydride (NaBH$_3$CN, 1.9 g, 30.24 mmole) was added thereto. The mixture was warmed to room temperature and then stirred. The reaction mixture was retained at pH 4 by adding portionwise the mixed solution of 6N HCl (20 ml) and methanol (30 ml) in the course of the reaction. After 5 hours, the reaction mixture was adjusted to pH 7 and distilled under reduced pressure to remove methanol. The remaining reaction solution was cooled down to 0° C., adjusted again to pH 11, saturated with sodium chloride and then extracted four times with chloroform. The extract was dried over anhydrous magnesium sulfate, filtered and concentrated to obtain the title compound (3.4 g, Yield: 58.3%).

$^1$H NMR(CDCl$_3$, ppm) δ: 7.20–5.00(bs, 1H), 3.56(m, 1H), 1.90–1.45(m, 9H)

EXAMPLE 10

Synthesis of (S)-N-cyclopentyl-N-hydroxy-3-(4-amidrazonophenyl)-2-(2-naphthylsulfonylamino) propionamide The compound prepared in Preparation 5 was treated according to the same procedure as Preparations 2 and 3 to obtain the intermediate (S)-N-cyclopentyl-N-hydroxy-3-(4-cyanophenyl)-2-(2-naphthylsulfonylamino)propionamide (0.1 g). This intermediate compound was used as the starting material and treated according to the same procedure as Example 1 to obtain the purified title compound (0.07 g, Yield: 63.6%).

$^1$H NMR(CD$_3$OD, ppm) δ: 8.25–7.30(m, 11H), 4.75(m, 1H), 4.30(m, 1H), 3.10, 2.75(m, m, 2H), 1.70–1.00(m, 8H)

Mass(FAB, m/e): 496(M$^+$+1)

EXAMPLE 11

Synthesis of (S)-N-cyclopentyl-N-(2-hydroxyethyl)-3-[4-amidrazonophenyl]-2-(2-naphthylsulfonylamino)pronionamide The compound (0.15 g, 0.24 mmole) prepared in Example 4 was dissolved in methanol (10 ml) and then palladium hydroxide (0.02 g) was added thereto. Hydrogen balloon was attached to the reaction vessel. After stirring for 2 days, the reaction mixture was filtered through a celite bed and concentrated. The residue was purified by HPLC to obtain the title compound (0.08 g, Yield: 63.7%). HPLC condition was identical to that used in Example 1.

$^1$H NMR(CD$_3$OD, ppm) δ: 7.80–7.00(m, 11H), 4.47(m, 1H), 4.00(m, 1H), 3.60(m, 2H), 3.10–2.70(m, 4H), 1.70–1.10(m, 8H)

Mass(FAB, m/e): 524(M$^+$+1)

EXAMPLE 12

Synthesis of (S)-N-cyclopentyl-N-methyl-3-[4-(methylamidino)phenyl]-2-(4-methoxy-2,3,6-trimethylbenzenesulfonylamino)propionamide The same procedure as Example 9, except that methylamine, instead of hydrazine, was added over three times at an interval of one hour, was carried out to obtain the purified title compound (0.08 g, Yield: 28.3%).

¹H NMR(CD₃OD, ppm) δ: 7.65(d, 2H), 7.40(dd, 2H), 6.70(d, 1H), 4.40, 3.90(m, m, 2H), 3.85(d, 3H), 3.20–2.90 (m, 5H), 2.55(m, 9H), 2.10(s, 3H), 1.75–0.90(m, 8H)

Mass(FAB, m/e): 515(M⁺+1)

EXAMPLE 13

Synthesis of (S)-N,N-dimethyl-3-(4-amidrazonophenyl)-2-(2-naphthylsulfonylamino)pronionamide The same procedure as Preparations 2 and 3, except that dimethylamine was used, was carried out to obtain the intermediate (S)-N,N-dimethyl-3-(4-cyanophenyl)-2-(2-naphthylsulfonylamino)-propionamide (0.11 g). This intermediate compound was used as the starting material and treated according to the same procedure as Example 1 to obtain the purified title compound (0.080 g, Yield: 53%).

¹H NMR(CD₃OD, ppm) δ: 2.19(s, 3H), 2.62(s, 3H), 2.70–2.95(m, 2H), 4.41(m, 1H), 7.20–8.30(m, 11H)

Mass(FAB, m/e): 440(M⁺+1)

EXAMPLE 14

Synthesis of (S)-N,N-dimethyl-3-[4-(methylamidino)phenyl]-2-(2-naphthylsulfonylamino)propionamide The same procedure as Example 13, except that instead of hydrazine in the procedure of Example 1, methylamine is added over three times at an interval of one hour, was carried out to obtain the purified title compound (0.10 g, Yield: 48%).

¹H NMR(CD₃OD, ppm) δ: 2.31(s, 3H), 2.75(s, 3H), 2.80–3.05(m, 2H), 3.07(s, 3H), 4.54(m, 1H), 7.30–8.40(m, 11H)

Mass(FAB, m/e): 439(M⁺+1)

EXAMPLE 15

Synthesis of (S)-N-cyclohexyl-N-methyl-3-(4-amidrazonophenyl)-2-(2-naphthylsulfonylamino)propionamide The same procedure as Preparation 1, except that cyclohexanone was used instead of cyclopentanone, was carried out to obtain cyclohexyl-methylamine hydrochloride, which was then treated according to the same procedure as Preparations 2 and 3 to obtain the intermediate (S)-N-cyclohexyl-N-methyl-3-(4-cyanophenyl)-2-(2-naphthylsulfonylamino)propionamide (0.21 g). This intermediate compound was used as the starting material and treated according to the same procedure as Example 1 to obtain the purified title compound (0.17 g, Yield: 73.9%).

¹H NMR(CD₃OD, ppm) δ: 8.32(d, 1H), 7.95(m, 3H), 7.75–7.53(m, 5H), 7.40(dd, 2H), 4.50, 4.21, 3.62(m, m, m, 2H), 3.05(m, 1H), 2.90(m, 1H), 2.55, 2.40(s, s, 3H), 1.80–0.62(m, 10H)

Mass(FAB, m/e): 508(M⁺+1)

EXAMPLE 16

Synthesis of (S)-N-cyclopropyl-N-methyl-3-(4-amidrazonophenyl)-2-(2-naphthylsulfonylamino)propionamide The same procedure as Preparation 1, except that cyclopropanone was used instead of cyclopentanone, was carried out to obtain cyclopropyl-methylamine hydrochloride, which was then treated according to the same procedure as Preparations 2 and 3 to obtain the intermediate (S)-N-cyclopropyl-N-methyl-3-(4-cyanophenyl)-2-(2-naphthylsulfonylamino)propionamide (0.21 g). This intermediate compound was used as the starting material and treated according to the same procedure as Example 1 to obtain the purified title compound (0.06 g, Yield: 12%).

¹H NMR(CD₃OD, ppm) δ: 0.40–0.90(m, 4H), 2.40(s, 3H), 2.75(m, 1H), 2.95(m, 1H), 7.20–8.30(m, 11H)

Mass(FAB, m/e): 466(M⁺+1)

PREPARATION 6

Synthesis of (S)-3-(4-cyanophenyl)-N-cyclopentyl-N-methyl-2-(2-naphthalen-1-yl-acetylamino)-propionamide The compound (0.51 g, 1.34 mmole) prepared in Preparation 2 was dissolved in 3 ml of dichloromethane and cooled down to −10° C., and then trifluoroacetic acid (TFA, 3 ml) was added thereto. The reaction mixture was stirred for 5 minutes, slowly warmed to room temperature, stirred again for 30 minutes and then distilled under reduced pressure to remove the volatile substance. The residue was dried using a vacuum pump and then DMF (10 ml) was added thereto. This solution was cooled to −10° C., and 1-(3-dimethylaminopropyl)-3-ethylcarbodiimide hydrochloride (EDC, 0.4 g) and 1-hydroxybenzotriazole (HOBT, 0.2 g) were added thereto and then stirred until they are completely dissolved. To the resulting solution were added 1-naphthalene acetic acid (0.26 g, 1.4 mmole) and N,N-diisopropylethylamine (1.2 ml). The reaction mixture was slowly warmed to room temperature and stirred for 3 hours. Upon completion of the reaction, the reaction solution was distilled under reduced pressure to remove the volatile substance. The residue was diluted with ethyl acetate, washed successively with aqueous saturated sodium hydrogen carbonate solution, dilute hydrochloric acid and brine, dried over anhydrous magnesium sulfate and then filtered. The filtrate was concentrated and the residue was purified by column chromatography (methanol:chloroform=1:99 (v/v)) to obtain the title compound (0.42 g, Yield: 68%).

¹H NMR(CDCl₃, ppm) δ: 8.0–6.8(m, 11H), 6.5(m, 1H), 5.1–5.3(m, 1H), 4.8–4.2(m, 1H), 4.1–3.8(m, 2H), 3.0–2.6 (m, 5H), 1.8–1.3(m, 8H)

EXAMPLE 17

Synthesis of (S)-3-[4-(amidrazono)phenyl]-N-cyclopentyl-N-methyl-2-(2-naphthalen-1-yl-acetylamino)propionamide The compound (0.21 g, 0.48 mmole) prepared in Preparation 6 was dissolved in pyridine (3 ml) and the resulting solution was introduced into a branched flask, to which triethylamine (0.2 ml) was added. The reaction flask was equipped so that hydrogen sulfide (H₂S) gas can be slowly introduced through one branch of the flask and discharged through another branch. The reaction solution was saturated with hydrogen sulfide gas while stirring for about 10 minutes, during which the colorless solution was changed into green color and then gradually into dark brown. The flask was closed with rubber stopper and allowed to stand for 3 days at room temperature to complete the reaction. Then, the reaction solution was distilled under reduced pressure to remove the volatile substance and dried by means of a vaccum pump. To the obtained yellow solid were added acetone (10 ml) and iodomethane (CH₃I, 0.3 ml) together and the mixture was heated under reflux for 30 minutes. This reaction mixture was distilled again under reduced pressure to remove the volatile substance and dried by means of a vaccum pump. The residue was dissolved in absolute methanol (5 ml) and then stirred. To this mixture was added portionwise 80% hydrazine hydrate (H₂NNH₂.H₂O, 0.04 ml, 0.72 mmole) over three times at an interval of 10 minutes. After the reaction is completed, the reaction solution was concentrated and then purified by HPLC to obtain the title compound (0.16 g, Yield: 70%).

¹H NMR(CD₃OD, ppm) δ: 8.0–7.3(m, 11H), 5.3–5.1(m, 1H), 4.8–4.2(m, 1H), 3.9(s, 2H), 3.2–2.9(m, 2H), 2.78, 2.72(2s, 3H), 1.8–1.3(m, 8H)

Mass(FAB, m/e): 472(M⁺+1)

EXAMPLE 18

Synthesis of (S)-3-[4-(amidrazono)-phenyl]-N-cyclopentyl-N-methyl-2-(5-dimethylamino-naphthalene-1-sulfonylamino)-propionamide The same procedure as Preparation 3, except that 5-(N,N-dimethylamino)-1-naphthalenesulfonyl chloride was used instead of 2-naphthalenesulfonyl chloride, was carried out to obtain the intermediate (S)-3-(4-cyanophenyl)-N-cyclopentyl-N-methyl-2-(5-dimethylamino-naphthalene-1-sulfonylamino)-propionamide (0.55 g, 1.09 mmole). This intermediate compound was then treated according to the same procedure as Example 1 to obtain the purified title compound (0.35 g, Yield: 60%).

¹H NMR(CD₃OD, ppm) δ: 8.6–7.3(m, 10H), 4.6–3.9(m, 2H), 3.11 (s, 3H), 3.0(s, 3H), 3.05–2.8(m, 2H), 2.5, 2.4(2s, 3H), 1.7–0.9(m, 10H)

Mass(FAB, m/e): 537(M⁺+1)

EXAMPLE 19

Synthesis of (S)-3-[4-(amidrazono)-phenyl]-N-cyclopentyl-N-methyl-2-(5-methoxy-naphthalene-1-sulfonylamino)-propionamide The same procedure as Preparation 3, except that 5-methoxy-1-naphthalenesulfonyl chloride was used instead of 2-naphthalenesulfonyl chloride, was carried out to obtain the intermediate (S)-3-(4-cyanophenyl)-N-cyclopentyl-N-methyl-2-(5-methoxy-naphthalene-1-sulfonylamino)-propionamide (0.18 g, 0.37 mmole). This intermediate compound was then treated according to the same procedure as Example 1 to obtain the purified title compound (0.12 g, Yield: 65%).

¹H NMR(CD₃OD, ppm) δ: 8.5–7.0(m, 10H), 4.6–4.0(m, 2H), 4.2(s, 3H), 3.0–2.8(m, 2H), 2.48–2.45(2s, 3H), 1.7–1.0 (m, 8H)

Mass(FAB, m/e): 523(M⁺+1)

EXAMPLE 20

Synthesis of (S)-3-[4-(amidrazono)-phenyl]-N-cyclopentyl-N-methyl-2-(6,7-dimethoxy-naphthalene-2-sulfonylamino)-propionamide The same procedure as Preparation 3, except that 6,7-dimethoxy-2-naphthalenesulfonyl chloride was used instead or 2-naphthalenesulfonyl chloride, was carried out to obtain the intermediate (S)-3-(4-cyanophenyl)-N-cyclopentyl-N-methyl-2-(6,7-dimethoxy-naphthalene-2-sulfonylamino)-propionamide (2.2 g, 2.2 mmole). This intermediate compound was then treated according to the same procedure as Example 1 to obtain the purified title compound (1.55 g, Yield: 67%).

¹H NMR(CD₃OD, ppm) δ: 8.4–7.3(m, 9H), 4.7–4.0(m, 2H), 4.2–4.0(2s, 6H), 3.2–2.8(m, 2H), 2.6–2.2 (2s, 3H), 1.7–1.0(m, 8H)

Mass(FAB, m/e): 554(M⁺+1)

EXAMPLE 21

Synthesis of (S)-3-[4-(methylamidino)-phenyl]-N-cyclopentyl-N-methyl-2-(5-dimethylamino-naphthalene-1-sulfonylamino)-propionamide The same procedure as Preparation 3, except that 5-(N,N-dimethylamino)-1-naphthalenesulfonyl chloride was used instead of 2-naphthalenesulfonyl chloride, was carried out to obtain the intermediate (S)-3-(4-cyanophenyl)-N-cyclopentyl-N-methyl-2-(5-dimethylamino-naphthalene-1-sulfonylamino)-propionamide (0.3 g, 0.6 mmole). This intermediate compound was then treated according to the same procedure as Example 1, except that methylamine is used instead of 80% hydrazine hydrate, to obtain the purified title compound (0.08 g, Yield: 25%).

¹H NMR(CD₃OD, ppm) δ: 8.52–7.25(m, 10H), 4.55–4.42 (m, 2H), 4.23–3.98(m, 2H), 3.09(s, 3H), 3.06–2.80(m, 2H), 2.90(m, 6H), 2.45(s, 3H), 2.38(s, 3H), 1.76–0.90(m, 8H)

Mass(FAB, m/e): 536(M⁺+1)

EXAMPLE 22

Synthesis of (S)-3-[4-(amidrazono)-phenyl]-N-cyclopentyl-N-methyl-2-(naphthalene-1-sulfonylamino)-propionamide The same procedure as Preparation 3, except that 1-naphthalenesulfonyl chloride was used instead of 2-naphthalenesulfonyl chloride, was carried out to obtain the intermediate (S)-3-(4-cyanophenyl)-N-cyclopentyl-N-methyl-2-(naphthalene-1-sulfonylamino)-propionamide (0.5 g, 1 mmole). This intermediate compound was then treated according to the same procedure as Example 1 to obtain the purified title compound (0.2 g, Yield: 40%).

¹H NMR(CD₃OD, ppm) δ: 8.61–7.28(m, 11H), 4.55–4.41 (m, 2H), 4.23–4.00(m, 2H), 3.00–2.84(m, 2H), 2.49, 2.41 (2s,3H), 1.70–1.00(m, 8H)

Mass(FAB, m/e): 494(M⁺+1)

EXAMPLE 23

Synthesis of (S)-3-[4-(amidrazono)-phenyl]-N-cyclopentyl-N-methyl-2-[2-(naphthalen-1-yl-oxy) acetylamino]-propionamide The same procedure as Preparation 6, except that (1-naphthoxy)acetic acid was used instead of 1-naphthalene acetic acid, was carried out to obtain the intermediate (S)-3-(4-cyanophenyl)-N-cyclopentyl-N-methyl-2-[2-(naphthalen-1-yloxy)-acetylamino]-propionamide (0.59 g, 1.3 mmole). This intermediate compound was then treated according to the same procedure as Example 17 to obtain the purified title compound (0.38 g, Yield: 60%).

¹H NMR(CD₃OD, ppm) δ: 8.25–6.8(m, 11H), 5.38–5.22 (m, 2H), 4.77–4.39(m, 2H), 4.70(s, 2H), 3.21–3.05(m, 2H), 2.88–2.77(2s, 3H), 1.92–1.40(m, 8H)

Mass(FAB, m/e): 488(M⁺+1)

EXAMPLE 24

Synthesis of (S)-3-[4-(amidrazono)-phenyl]-N-cyclopentyl-N-methyl-2-[2-(naphthalen-2-yl-oxy) acetylamino]-propionamide The same procedure as Preparation 6, except that (2-naphthoxy)acetic acid was used instead of 1-naphthalene acetic acid, was carried out to obtain the intermediate (S)-3-[4-(amino-hydrazonomethyl)-phenyl]-N-cyclopentyl-N-methyl-2-[2-(naphthalen-2-yl-oxy)acetylamino]-propionamide (0.7 g, 1.54 mmole). This intermediate compound was then treated according to the same procedure as Example 17 to obtain the purified title compound (0.59 g, Yield: 63%).

$^1$H NMR(CD$_3$OD, ppm) δ: 7.80–7.14(m, 11H), 5.35–5.18 (m, 1H), 4.76–4.35(m, 1H), 4.61(s, 2H), 3.18–3.05(m, 2H), 2.85–2.75(2s, 3H), 1.85–1.25(m, 8H)

Mass(FAB, m/e): 488(M$^+$+1)

PREPARATION 7

Synthesis of N-t-butoxycarbonyl-N-methylaminoacetic Acid Methyl Ester

Glycine methyl ester hydrochloride (1.0 g, 8.2 mmole) was dissolved in water (12 ml) and 1N aqueous sodium hydroxide solution (8.2 ml), and then 1,4-dioxane (20 ml) was added thereto. To this mixture was added di-t-butyldicarbonate (2.2 g, 9.8 mmole) at 0° C., and the mixture was warmed to room temperature and stirred for 2 hours. The volatile substance was removed from the reaction mixture under reduced pressure and the residue was diluted with ethyl acetate, washed successively with aqueous saturated sodium hydrogen carbonate solution, dilute hydrochloric acid and saturated saline, dried over anhydrous sodium sulfate, filtered and then concentrated. The resulting product was dissolved in dimethylformamide (DMF, 10 ml). To this solution was slowly added 60% sodium hydride (NaH, 0.25 g, 6.4 mmole) at 0° C. and then added dropwise iodomethane (CH$_3$I, 1.1 ml). The mixture was slowly warmed to room temperature and stirred for 3 hours at the same temperature. The mixture was filtered through a Celite bed and concentrated under reduced pressure. The residue was diluted with ethyl acetate, washed successively with aqueous saturated sodium hydrogen carbonate solution, dilute hydrochloric acid and brine, dried over anhydrous sodium sulfate, filtered and then concentrated. The residue was purified by column chromatography using ethyl acetate/hexane (6/4, by volume) as an eluent to obtain the purified title compound (1.0 g, Yield: 65%).

$^1$H NMR(CDCl$_3$, ppm) δ: 1.45(d, 9H), 2.95(s, 3H), 3.78 (s, 3H), 3.92(s, 1H), 4.00(s, 1H)

Mass(FAB, m/e): 204(M+1)

PREPARATION 8

Synthesis of {[(S)-2-(t-butoxtcarbonylamino)-3-(4-cyanophenyl)propionyl]-methylamino}-acetic acid methyl ester (S)-2-(t-butoxycarbonylamino)-3-(4-cyanophenyl) propionic acid (0.5 g, 1.72 mmole) was dissolved in dimethylformamide (DMF). The resulting solution was cooled down to 0° C., and then 1-(3-dimethylaminopropyl)-3-methylcarbodiimide hydrochloride (EDC, 0.39 g) and 1-hydroxybenzotriazole (HOBT, 0.28 g) were added thereto and stirred until they are completely dissolved. Separately, the compound (0.35 g, 1.72 mmole) prepared in Preparation 7 was dissolved in dichloromethane (2 ml) and cooled down to −10° C. Trifluoroacetic acid (2 ml) was added thereto and the mixture was stirred for 5 minutes, slowly warmed to room temperature, stirred again for 30 minutes and then distilled under reduced pressure to remove the volatile substance. The resulting compound thus prepared and N-methylmorpholine (1 ml) were added to the solution as obtained above, and then the reaction solution was slowly warmed to room temperature and stirred for 3.5 hours. Upon completion of the reaction, the reaction solution was distilled under reduced pressure to remove the volatile substance. The residue was diluted with ethyl acetate, washed successively with aqueous saturated sodium hydrogen carbonate solution, dilute hydrochloric acid and brine, dried over anhydrous sodium sulfate, filtered and then concentrated. The residue was purified by column chromatography using ethyl acetate/hexane (3/7, by volume) as an eluent to obtain the purified title compound (0.58 g, Yield: 90%).

$^1$H NMR(CDCl$_3$, ppm) δ: 1.40(m, 9H), 3.08(s, 3H), 2.95–3.25(m, 2H), 3.78(s, 3H), 3.89–4.35(m, 2H), 4.95(m, 1H), 5.52(d, 1H), 7.35(m, 2H), 7.60(m, 2H)

Mass(FAB, m/e): 376(M+1)

PREPARATION 9

Synthesis of 1-{[3-(4-cyanophenyl)-(S)-2-(naphthalene-2-sulfonylamino)-propionyl]-methylamino}-acetic acid methyl ester The compound (0.57 g, 1.52 mmole) prepared in Preparation 8 was dissolved in dichloromethane (2 ml) and cooled down to −10° C., and then trifluoroacetic acid (TFA, 2 ml) was added thereto. The reaction mixture was stirred for 5 minutes, slowly warmed to room temperature, stirred again for 30 minutes and then distilled under reduced pressure to remove the volatile substance. The residue was dried using a vacuum pump and then DMF (10 ml) was added thereto. This solution was cooled down to −10° C. and N,N-diisopropylethylamine (1 ml) was added thereto. This reaction solution was warmed to room temperature and stirred for about 5 minutes and then 2-naphthalenesulfonyl chloride (0.41 g, 1.82 mmole) was added thereto. The reaction mixture was stirred for one hour to complete the reaction and distilled under reduced pressure to remove the volatile substance. The residue was diluted with ethyl acetate, washed two times with water, dried over anhydrous magnesium sulfate and then filtered. The filtrate was concentrated and the residue was purified by column chromatography using ethyl acetate/hexane (1/1, by volume) as an eluent to obtain the purified title compound (0.55 g, Yield: 78%).

$^1$H NMR(CDCl$_3$, ppm) δ: 2.88(s, 3H), 2.80–3.20(m, 2H), 3.80(d, 3H), 4.12(d, 2H), 4.58(m, 1H), 6.40(d, 1H), 7.20–8.40(m, 11H)

Mass(FAB, m/e): 466(M+1)

EXAMPLE 25

Synthesis of {[3-(4-amidrazono-phenyl)-(S)-2-(naphthalene-2-sulfonylamino)-propionyl]-methyl-amino}-acetic acid methyl ester The compound (0.55 g, 1.18 mmole) prepared in Preparation 9 was dissolved in pyridine (10 ml) and the resulting solution was introduced into a branched flask, to which triethylamine (0.45 ml) was added. The reaction flask was equipped so that hydrogen sulfide (H$_2$S) gas can be slowly introduced through one branch of the flask and discharged through another branch. The reaction solution was saturated with hydrogen sulfide gas, while stirring for about 10 minutes, during which the colorless solution was changed into green color and then gradually into dark brown. The flask was closed with rubber stopper and allowed to stand for 3 days at room temperature. Upon completion of the reaction, the reaction solution was distilled under reduced pressure to remove the volatile substance and dried by means of a vaccum pump. To the obtained yellow solid were added acetone (10 ml) and iodomethane (CH₃I, 0.55 ml) together and the mixture was heated under reflux for 30 minutes. This reaction mixture was distilled again under reduced pressure to remove the volatile substance and dried by means of a vaccum pump. The residue was dissolved in absolute methanol (5 ml) and then stirred. To this solution was added portionwise 80% hydrazine hydrate (H₂NNH₂.H₂O, 0.11 ml, 1.77 mmole) over three times at an interval of 10 minutes. After the reaction is completed, the reaction solution was concentrated and then purified by HPLC to obtain the title compound (0.25 g, Yield: 43%).

¹H NMR(CD₃OD, ppm) δ: 2.95(s, 3H), 2.70–3.20(m, 2H), 3.54(s, 3H), 3.80(d, 2H), 4.55(m, 1H), 7.20–8.30(m, 11H)

Mass(FAB, m/e): 498(M+1)

EXAMPLE 26

Synthesis of {[3-(4-amidrazono-phenyl)-(S)-2-(naphthalene-2-sulfonylamino)propionyl]-methyl-amino}-acetic acid The compound (160 mg, 0.32 mmole) prepared in Example 25 was dissolved in the mixed solvent (4 ml) of methanol and water (3:1). To this solution was slowly added lithium hydroxide hydrate (LiOH.H₂O, 0.016 g, 0.38 mmole) at 0° C. and the mixture was stirred for 2 hours at room temperature. Upon completion of the reaction, the reaction solution was concentrated and purified by HPLC to obtain the title compound (50 mg, Yield: 32%).

¹H NMR(CD₃OD, ppm) δ: 2.20–2.60(m, 2H), 2.48(s, 3H), 2.78(s, 3H), 2.32(m, 2H), 4.12(m, 1H), 6.80–7.80(m, 11H)

Mass(FAB, m/e): 484(M+1)

EXAMPLE 27

Synthesis of (S)-2-{[3-(4-amidrazono-phenyl)-(S)-2-(naphthalene-2-sulfonylamino)-propionyl]-methyl-amino}-propionic acid methyl ester The same procedure as Preparation 7, except that (L)-alanine methyl ester was used instead of glycine methyl ester, was carried out to obtain (L)-(N-t-butoxycarbonyl-N-methyl)-alanine methyl ester, which was then treated according to the same procedure as Preparations 8 and 9 to obtain the intermediate (S)-2-{[3-(4-cyanophenyl)-(S)-2-(naphthalene-2-sulfonylamino)propionyl]-methyl-amino}-propionic acid methyl ester (1.43 g). This intermediate compound was treated according to the same procedure as Example 25 to obtain the purified title compound (0.64 g, Yield: 48%).

¹H NMR(CD₃OD, ppm) δ: 0.69, 0.88(d, d, 3H), 2.79, 2.95(s, s, 3H), 2.80, 3.06(m, m, 2H), 3.48, 3.57 (s, s, 3H), 4.29(m, 1H), 4.55(m, 1H), 7.30–8.30(m, 11H)

Mass(FAB, m/e): 512(M+1)

EXAMPLE 28

Synthesis of (S)-2-{[3-(4-amidrazono-phenyl)-(S)-2-(naphthalene-2-sulfonylamino)-propionyl]-methyl-amino}-propionic acid The compound prepared in Example 27 was treated according to the same procedure as Example 26 to obtain the purified title compound (0.06 g, Yield: 41%).

¹H NMR(CD₃OD, ppm) δ: 0.64, 0.95(d, d, 3H), 2.76, 2.92(s, s, 3H), 2.83, 3.09(m, m, 2H), 4.37(m, 1H), 4.54(m, 1H), 7.30–8.40(m, 11H)

Mass(FAB, m/e): 498(M+1)

EXAMPLE 29

Synthesis of (R)-2-{[3-(4-amidrazono-phenyl)-(S)-2-(naphthalene-2-sulfonylamino)-propionyl]-methyl-amino}-propionic acid methyl ester The same procedure as Preparation 7, except that (D)-alanine methyl ester is used instead of glycine methyl ester, was carried out to obtain (D)-(N-t-butoxycarbonyl-N-methyl)-alanine methyl ester, which was then treated according to the same procedure as Preparations 8 and 9 to obtain the intermediate (R)-2-{[3-(4-cyanophenyl)-(S)-2-(naphthalene-2-sulfonylamino)propionyl]-methyl-amino}-propionic acid methyl ester (0.78 g). This intermediate compound was treated according to the same procedure as Example 25 to obtain the purified title compound (0.58 g, Yield: 70%).

¹H NMR(CD₃OD, ppm) δ: 0.89, 1.21(d, d, 3H), 2.46, 2.94(s, s, 3H), 2.80, 3.08(m, m, 2H), 3.49, 3.78 (s, s, 3H), 4.29(m, 1H), 4.59(m, 1H), 7.30–8.40(m, 11H)

Mass(FAB, m/e): 512(M+1)

EXAMPLE 30

Synthesis of (R)-2-{[3-(4-amidrazono-phenyl)-(S)-2-(naphthalene-2-sulfonylamino)-propionyl]-methyl-amino}-propionic acid The compound (0.03 g, 0.059 mmole) prepared in Example 29 was treated according to the same procedure as Example 26 to obtain the purified title compound (0.01 g, Yield: 33%).

¹H NMR(CD₃OD, ppm) δ: 0.90, 1.18(d, d, 3H), 2.44, 2.92(s, s, 3H), 2.82, 3.08(m, m, 2H), 4.33(m, 1H), 4.62(m, 1H), 7.30–8.40(m, 11H)

Mass(FAB, m/e): 498(M+1)

EXAMPLE 31

Synthesis of (R) -2-{[3-(4-amidrazono-phenyl)-(S)-2-(naphthalene-2-sulfonylamino)-propionyl]-methyl-amino}-3-methyl-butyric acid methyl ester The same procedure as Preparation 7, except that (D)-valine methyl ester was used instead of glycine methyl ester, was carried out to obtain (D)-(N-t-butoxycarbonyl-N-methyl)-valine methyl ester, which was then treated according to the same procedure as Preparations 8 and 9 to obtain the intermediate (R)-2-{[3-(4-cyanophenyl)-(S)-2-(naphthalene-2-sulfonylamino)propionyl]-methyl-amino}-3-methyl-butyric acid methyl ester (0.19 g). This intermediate compound was treated according to the same procedure as Example 25 to obtain the purified title compound (0.11 g, Yield: 55%).

¹H NMR(CD₃OD, ppm) δ: 0.59, 0.70(d, d, 3H), 0.89, 0.98(d, d, 3H), 2.09, 2.21(m, m, 1H), 2.75, 3.06 (s, s, 3H), 3.40, 3.68(s, s, 3H), 4.34, 4.38(d, d, 1H), 4.63, 4.70(m, m, 1H), 7.20–8.40(m, 11H)

Mass(FAB, m/e): 540(M⁺+1)

EXAMPLE 32

Synthesis of (R)-2-{[3-(4-amidrazono-phenyl)-(S)-2-(naphthalene-2-sulfonylamino)-propionyl]-methyl-amino}-3-methyl-butyric acid The compound prepared in Example 31 was treated according to the same procedure as Example 26 to obtain the purified title compound (0.04 g, Yield: 40%).

$^1$H NMR(CD$_3$OD, ppm) δ: 0.57, 0.63(d, d, 3H), 0.92, 0.99(d, d, 3H), 2.09, 2.18(m, m, 1H), 2.74, 3.08 (s, s, 3H), 4.18, 4.36(d, d, 1H), 4.64, 4.70(m, m, 1H), 7.20–8.40(m, 11H)

Mass(FAB, m/e): 526(M+1)

EXAMPLE 33

Synthesis of 3-{[3-(4-amidrazono-phenyl)-(S)-2-(naphthalene-2-sulfonylamino)-propionyl]-methyl-amino}-propionic acid methyl ester The same procedure as Preparation 7, except that 3-aminopropionic acid methyl ester was used instead of glycine methyl ester, was carried out to obtain 3-(N-t-butoxycarbonyl-N-methyl)amino-propionic acid methyl ester, which was then treated according to the same procedure as Preparations 8 and 9 to obtain the intermediate 3-{[3-(4-cyanophenyl)-(S)-2-(naphthalene-2-sulfonylamino)-propionyl]-methyl-amino}-propionic acid methyl ester (0.69 g). This intermediate compound was treated according to the same procedure as Example 25 to obtain the purified title compound (0.55 g, Yield: 74%).

$^1$H NMR(CD$_3$OD, ppm) δ: 8.31, 7.97, 7.68, 7.48(d, m, m, m, 11H), 4.62, 4.51(m, m, 1H), 3.62, 3.55 (s, s, 3H), 3.05, 2.85(m, m, 4H), 2.80, 2.45(s, s, 3H), 2.38, 1.91(m, m, 2H)

Mass(FAB, m/e): 512(M$^+$+1)

EXAMPLE 34

Synthesis of 3-{[3-(4-amidrazono-phenyl)-(S)-2-(naphthalene-2-sulfonylamino)-propionyl]-methyl-amino}-propionic acid The compound prepared in Example 33 was treated according to the same procedure as Example 26 to obtain the purified title compound (0.17 g, Yield: 321).

$^1$H NMR(CD$_3$OD, ppm) δ: 8.31, 7.98, 7.78–7.37(d, m, m, 11H), 4.65, 4.52(m, m, 1H), 3.20–2.85(m, 4H1), 2.80, 2.45(s, s, 3H), 2.38, 1.91(m, m, 2H)

Mass(FAB, m/e): 498(M +1)

EXAMPLE 35

Synthesis of 4-{[3-(4-amidrazono-phenyl)-(S)-2-(naphthalene-2-sulfonylamino)-propionyl]-methyl-amino}-butyric acid methyl ester The same procedure as Preparation 7, except that 4-aminobutyric acid methyl ester was used instead of glycine methyl ester, was carried out to obtain 4-(N-t-butoxycarbonyl-N-methyl)amino-propionic acid methyl ester, which was then treated according to the same procedure as Preparations 8 and 9 to obtain the intermediate 4-{13-(4-cyanophenyl)-(S)-2-(naphthalene-2-sulfonylamino)-propionyl]-methylamino}-butyric acid methyl ester (0.51 g). This intermediate compound was treated according to the same procedure as Example 25 to obtain the purified title compound (0.40 g, Yield: 74%).

$^1$H NMR(CD$_3$OD, ppm) δ: 8.32(s, 11), 7.98(m, 3H), 7.78–7.36(m, 7H), 4.55(m, 1H), 3.72, 3.60(s, s, 3H), 3.10, 2.81(m, m, 4H), 2.79, 2.55(s, s, 3H), 2.22(m, 1H), 1.89(m, 11), 1.63, 1.42 (m, m, 1H) , 1.18 (m, 1H)

Mass(FAB, m/e): 526(M$^+$+1)

EXAMPLE 36

Synthesis of 4-{[3-(4-amidrazono-phenyl)-(S)-2-(naphthalene-2-sulfonylamino)-propionyl]-methyl-amino}-butyric acid The compound prepared in Example 35 was treated according to the same procedure as Example 26 to obtain the purified title compound (0.12 g, Yield: 32%).

$^1$H NMR(CD$_3$OD, ppm) δ: 8.32(m, 1H), 7.98(m, 3H), 7.78–7.35(m, 7H), 4.55(m, 1H), 3.05, 2.81(m, m, 4H), 2.79, 2.50(s, s, 3H), 2.18(m, 11H), 1.89 (m, 1H), 1.35(m, m, 1H), 1.16(m, 1H)

Mass(FAB, m/e): 512(M$^+$+1)

PREPARATION 10

Synthesis of N-t-butoxycarbonyl-N-cyclopropyl-acetic acid methyl ester

Cyclopropylamine (1.34 g, 23.49 mmole) was mixed with DMF (15 ml) and triethylamine (3 ml) and the mixture was introduced into the reaction vessel. Methylbromoacetate (2.2 ml, 23.49 mmole) and DMF (5 ml) were introduced into the dropping funnel. The reaction vessel was cooled to 0° C. and then the solution contained in the dropping funnel was added dropwise to the reaction vessel. Upon completion of the addition, the reaction mixture was warmed to room temperature and allowed to react for 3.5 hours. After the reaction is completed, water (10 ml) and 3N sodium hydroxide (8 ml) were added thereto. To the reaction mixture was added 1,4-dioxane (10 ml) followed by the addition of butyloxycarbonyl anhydride (6.1 g, 27.95 mmole). The reaction mixture was allowed to react for 3 hours at room temperature and distilled under reduced pressure to remove the volatile substance. The residue was diluted with ethyl acetate and washed successively with saturated sodium hydrogen carbonate, dilute hydrochloric acid and brine. The organic layer was separated, dried over anhydrous magnesium sulfate and filtered. The solvent was removed under reduced pressure from the filtrate. The residue was purified by column chromatography (eluent: ethyl acetate/hexane (6/4, by volume)) to obtain the purified title compound (2.3 g, Yield: 43%).

$^1$H NMR(CDCl$_3$, ppm) δ: 3.95(m, 2H), 3.72(m, 3H), 2.75, 2.52 (bs, bs, 1H), 1.45, 1.47(s, s, 9H), 0.80–0.45(m, 4H)

Mass(FAB, m/e): 230(M$^+$+1)

EXAMPLE 37

Synthesis of {[3-(4-amidrazono-phenyl)-(S)-2-(naphthalene-2-sulfonylamino)-propionyl]-cyclopropylamino}-acetic acid methyl ester The compound prepared in Preparation 10 was treated according to the same procedure as Preparations 8 and 9 to obtain the intermediate {[3-(4-cyanophenyl)-(S)-2-(naphthalene-2-sulfonylamino)-propionyl]-cyclopropylamino}-acetic acid methyl ester (0.30 g). This intermediate compound was treated according to the same procedure as Example 25 to obtain the purified title compound (0.25 g, Yield: 77%).

$^1$H NMR(CD$_3$OD, ppm) δ: 8.24(s, 1H), 7.93(m, 3H), 7.65(m, 3H), 7.42(d, 2H), 7.35(d, 2H), 5.02(m, 1H), 3.92(d, 1H), 3.64(d, 1H), 3.60(s, 3H), 3.19(dd, 1H), 2.80(m, 2H), 0.95, 0.85, 0.61(m, m, m, 4H)

Mass(FAB, m/e): 524(M$^+$+1)

EXAMPLE 38

Synthesis of {[3-(4-amidrazono-phenyl)-(S)-2-(naphthalene-2-sulfonylamino)-propionyl-cyclopropylamino}-acetic acid The compound prepared in Example 37 was treated according to the same procedure as Example 26 to obtain the purified title compound (0.07 g, Yield: 29%).

$^1$H NMR(CD$_3$OD, ppm) δ: 8.24(s, 1H), 7.93(m, 3H), 7.42(d, 2H), 7.35(d, 2H), 5.02(m, 1H), 3.95(d, 1H), 3.54(d, 1H), 3.20(dd, 1H), 2.80(m, 2H), 0.95, 0.85, 0.61(m, m, m, 4H)

Mass(FAB, m/e): 510(M$^+$+1)

EXAMPLE 39

Synthesis of {[3-(4-amidrazono-phenyl)-(S)-2-(naphthalene-2-sulfonylamino)-propionyl]-butylamino}-acetic acid methyl ester The same procedure as Preparation 10, except that butylamine was used instead of cyclopropylamine, was carried out to obtain N-t-butoxycarbonyl-N-butylamino-acetic acid methyl ester, which was then treated according to the same procedure as Preparations 8 and 9 to obtain the intermediate {(3-(4-cyano-phenyl)-(S)-2-(naphthalene-2-sulfonylamino)-propionyl]-butylamino}-acetic acid methyl ester (0.31 g). This intermediate compound was treated according to the same procedure as Example 25 to obtain the purified title compound (0.19 g, Yield: 58%).

$^1$H NMR(CD$_3$OD, ppm) 6: 8.30–7.32(m, 1H), 4.32–4.09 (m, 3H), 3.55(s, 3H), 3.57–2.50(m, 4H), 1.26–0.50(m, 7H)

Mass(FAB, m/e): 540(M$^+$+1)

EXAMPLE 40

Synthesis of {[3-(4-amidrazono-phenyl)-(S)-2-(naphthalene-2-sulfonylamino)-propionyl]-butylamino}-acetic acid The compound prepared in Example 39 was treated according to the same procedure as Example 26 to obtain the purified title compound (0.12 g, Yield: 67%).

$^1$H NMR(CD$_3$OD, ppm) δ: 8.30–7.10(m, 11H), 4.31–4.10 (m, 3H), 3.52–2.55(m, 4H), 1.25–0.50(m, 7H)

Mass(FAB, m/e): 526(M+1)

EXAMPLE 41

Synthesis of {[3-(4-amidrazono-Phenyl)-(5)-2-(naphthalene-2-sulfonylamino)-propionyl]-cyclopentylamino}-acetic acid methyl ester The same procedure as Preparation 10, except that cyclopentylamine was used instead of cyclopropylamine, was carried out to obtain N-t-butoxycarbonyl-N-cyclopentylamino-acetic acid methyl ester, which was then treated according to the same procedure as Preparations 8 and 9 to obtain the intermediate {[3-(4-cyanophenyl)-(S)-2-(naphthalene-2-sulfonylamino)-propionyl]-cyclo-pentylamino}-acetic acid methyl ester (0.23 g). This intermediate compound was treated according to the same procedure as Example 25 to obtain the purified title compound (0.12 g, Yield: 50%).

$^1$H NMR(CD$_3$OD, ppm) δ: 8.35–7.35(m, 11H), 4.66, 4.33(m, m, 1H), 4.15(m, 1H), 3.75, 3.53(m, m, 1H), 3.61(s, 3H), 3.40–2.80(m, 3H), 1.90–0.60(m, 8H)

Mass(FAB, m/e): 552(M$^+$+1)

EXAMPLE 42

Synthesis of {[3-(4-amidrazono-phenyl)-(S)-2-(naphthalene-2-sulfonylamino)-propionyl]-cyclopentylamino}-acetic acid The compound prepared in Example 41 was treated according to the same procedure as Example 26 to obtain the purified title compound (0.4 g, Yield: 33%).

$^1$H NMR(CD$_3$OD, ppm) δ: 8.35–7.35(m, 1H), 4.65, 4.32 (m, m, 1H), 4.15(m, 1H), 3.75, 3.52(m, m, 1H), 3.41, 3.28–3.10, 2.80(m, m, m, 3H), 1.90–0.60(m, 8H)

Mass(FAB, m/e): 538(M$^+$+1)

PREPARATION 11

Synthesis of 1-(N-t-butoxycarbonyl-N-methylamino)-cyclopentane carboxylic acid methyl ester Cycloleucine (3 g, 23.2 mmole) was dissolved in 1N aqueous sodium hydroxide solution (23.2 ml) and distilled water (7 ml), and then 1,4-dioxane (30 ml) was added thereto. To this mixture was added di-t-butyldicarbonate (6.1 g, 27.8 mmole) at 0° C., and the mixture was warmed to room temperature and then stirred for 2 hours. The volatile substance was removed from the reaction mixture under reduced pressure and the residue was diluted with ethyl acetate, washed successively with aqueous saturated sodium hydrogen carbonate solution, dilute hydrochloric acid and brine, dried over anhydrous sodium sulfate, filtered and then concentrated. The resulting white solid product was dissolved in dimethylformamide (DMF, 30 ml). To this solution was added potassium carbonate (4.8 g, 34.8 mmole) and then added dropwise iodomethane (CH$_3$I, 14.4 ml, 232 mmole). The reaction mixture was stirred for 2 hours at room temperature and distilled under reduced pressure to remove the volatile substance. The residual solution was diluted with ethyl acetate, washed successively with aqueous saturated sodium hydrogen carbonate solution, dilute hydrochloric acid and saturated saline, dried over anhydrous sodium sulfate, filtered and then concentrated. The resulting product was dissolved in dimethylformamide (DMF, 20 ml). To this solution was slowly added 60% sodium hydride (NaH, 0.46 g, 11.4 mmole) at 0° C. and then added dropwise iodomethane (CH$_3$I, 1.8ml, 28.4 mmole). The mixture was slowly warmed to room temperature and stirred for 3 hours at the same temperature. Water was added to the reaction mixture to remove the residual sodium hydride. The mixture was filtered and concentrated under reduced pressure. The residue was diluted with ethyl acetate, washed successively with aqueous saturated sodium hydrogen carbonate solution, dilute hydrochloric acid and saturated saline, dried over anhydrous sodium sulfate, filtered and then concentrated. The residue was purified by column chromatography using ethyl acetate/hexane (3/7, by volume) as an eluent to obtain the purified title compound (2.0 g, Yield: 34%).

$^1$H NMR(CDCl$_3$, ppm) δ: 1.35(s, 9H), 1.62(m, 4H), 1.78(m, 2H), 2.18(m, 2H), 2.90(s, 3H), 3.62(s, 3H)

Mass(FAB, m/e): 258(M+1)

EXAMPLE 43

Synthesis of 1-{[3-(4-amidrazono-phenyl)-(S)-2-(naphthalene-2-sulfonylamino)-propionyl]-methyl-amino}-cyclopentane carboxylic acid methyl ester The compound prepared in Preparation 11 was treated according to the same procedure as Preparations 8 and 9 to obtain the intermediate 1-{[3-(4-aminohydrazono-methyl)-phenyl-(S)-2-(naphthalene-2-sulfonylamino)-propionyl]-methylamino}-cyclopentane carboxylic acid methyl ester (0.28 g). This intermediate compound was treated according to the same procedure as Example 25 to obtain the purified title compound (0.56 g, Yield: 53%).

$^1$H NMR(CD$_3$OD, ppm) δ: 0.52(m, 1H), 0.89(m, 1H), 1.29(m, 2H), 1.52(m, 1H), 1.76(m, 2H), 2.05(m, 1H), 2.75, 3.00(m, m, 2H), 2.88(s, 3H), 3.50(s, 3H), 4.48(m, 1H), 6.38(m, 1H), 7.30–8.40(m, 11H)

Mass(FAB, m/e): 552(M+1)

EXAMPLE 44

Synthesis of 1-{[3-(4-amidrazono-phenyl)-(S-2-(naphthalene-2-sulfonylamino)-propionyl]-methylamino}-cyclopentane carboxylic acid The compound prepared in Example 43 was treated according to the same procedure as Example 26 to obtain the purified title compound (0.01 g, Yield: 17%).

$^1$H NMR(CD$_3$OD, ppm) δ: 0.42(m, 1H), 0.74(m, 1H), 1.25(m, 2H), 1.50(m, 1H), 1.78(m, 2H), 2.05(m, 1H), 2.75, 3.08(m, m, 2H), 2.98(s, 3H), 4.58(m, 1H), 7.40–8.40(m, 11H)

Mass(FAB, m/e): 538(M+1)

PREPARATION 12

Synthesis of 2-(N-t-butoxycarbonyl-N-methyl)-amino-cyclopentane carboxylic acid ethyl ester Ethyl 2-oxycyclopentane carboxylate (10 ml, 67.49 mmole) was introduced together with ethanol (100 ml) into a reaction vessel. Then, methylamine hydrochloride (4.69 g, 68.13 mmole) and water (10 ml) were added thereto to dissolve the reactants. To the reaction vessel was added sodium cyanoborohydride (4.3 g, 68.43 mmole), and the mixture was adjusted to pH 6 and then allowed to react for 12 hours or more at 30 to 40° C. The reaction mixture was then concentrated under reduced pressure, cooled down to 0° C., adjusted to pH 2 using 6N hydrochloric acid and washed three times with diethyl ether. The aqueous layer was adjusted again to pH 10 and the same amount of dioxane was added thereto. To this mixture was added 1 equivalent weight of butyloxycarbonyl anhydride. This reaction mixture was allowed to react for 3 hours at room temperature. After the reaction is completed, the reaction solution was distilled under reduced pressure to remove the volatile substance, diluted with ethyl acetate and washed successively with saturated sodium hydrogen carbonate, dilute hydrochloric acid and saturated saline. The organic layer was dried over anhydrous magnesium sulfate, filtered and distilled under reduced pressure to remove the solvent. The residue was purified by column chromatography (eluent= ethyl acetate:hexane=1:1 (v/v)) to obtain the purified title compound (5.82 g, Yield: 32%).

$^1$H NMR(CDCl$_3$, ppm) δ: 4.55(m, 1H), 4.10(m, 2H), 2.79(s, 3H), 2.73(s, 1H), 2.00–1.40(m, 6H), 1.45(s, 9H), 1.24(t, 3H)

Mass(FAB, m/e): 272(M$^+$+1)

EXAMPLE 45

Synthesis of 2-{[3-(4-amidrazono-phenyl)-(S)-2-(naphthalene-2 -sulfonylamino)-propionyl]-methylamino}-cyclopentane carboxylic acid ethyl ester The compound prepared in Preparation 12 was treated according to the same procedure as Preparations 8 and 9 to obtain the intermediate 2-{[3-(4-cyanophenyl)-(S)-2-(naphthalene-2-sulfonylamino)-propionyl]-methylamino}-cyclopentane carboxylic acid ethyl ester (0.48 g). This intermediate compound was then treated according to the same procedure as Example 25 to obtain the purified title compound (0.36 g, Yield: 71%).

$^1$H NMR(CD$_3$OD, ppm) δ: 8.39–7.25(m, 11H), 4.78–4.40 (m, 2H), 4.05(m, 2H), 3.05(m, 1H), 2.90–2.65(m, 3H), 2.50–2.40(m, 2H), 2.05, 1.90–1.30, 0.85(m, m, m, 6H), 1.28–1.15(m, 3H)

Mass(FAB, m/e): 566(M$^+$+1)

EXAMPLE 46

Synthesis of 2-{[3-(4-amidrazono-phenyl)-(S)-2-(naphthalene-2-sulfonylamino)-propionyl]-methylamino}-cyclopentane carboxylic acid The compound prepared in Example 45 was treated according to the same procedure as Example 26 to obtain the purified title compound (0.086 g, Yield: 25%).

$^1$H NMR(CD$_3$OD, ppm) δ: 8.39–7.20(m, 11H), 4.78–4.50 (m, m, 2H), 3.05(m, 1H), 2.90–2.40(m, 5H), 2.10, 1.90–1.20, 0.75(m, m, m, 6H)

Mass(FAB, m/e): 538(M$^+$+1)

EXAMPLE 47

Synthesis of (S)-2-{[3-(4-amidrazono-phenyl)-(S)-2-(naphthalene-2-sulfonylamino)-propionyl]-methyl-amino}-3-methyl-butyric acid methyl ester The same procedure as Preparation 7, except that (L)-valine methyl ester is used instead of glycine methyl ester, was carried out to obtain (L)-(N-t-butoxycarbonyl-N-methyl)-valine methyl ester, which was then treated according to the same procedure as Preparations 8 and 9 to obtain the intermediate (S)-2-{[3-(4-cyano-phenyl)-(S)-2-(naphthalene-2-sulfonylamino)-propionyl]-methylamino}-3-methyl-butyric acid methyl ester (0.13 g). This intermediate compound was treated according to the same procedure as Example 25 to obtain the purified title compound (0.09 g, Yield: 69%).

$^1$H NMR(CD$_3$OD, ppm) δ: 8.30, 7.95, 7.75–7.20(m, m, m, 11H), 4.75–4.25(m, 2H), 4.65, 3.39(m, m, 3H), 3.15–2.65 (m, 4H), 2.22, 2.15(s, s, 1H), 2.08, 1.90(m, m, 1H), 1.00–0.55, 0.20 (m, m, 6H)

Mass(FAB, m/e): 540(M$^+$+1)

EXAMPLE 48

Synthesis of 1-[3-(4-amidrazono-phenyl)-(S)-2-(naphthalene-2-sulfonylamino)-propionyl]-piperidine-(R)-2-carboxylic acid methyl ester The same procedure as Preparation 7, except that (D)-pipecolinic acid methyl ester was used instead of glycine methyl ester, was carried out and the resulting product was then treated according to the same procedure as Preparations 8 and 9 to obtain the intermediate 1-[3-(4-cyanophenyl)-(S)-2-(naphthalene-2-sulfonylamino)-propionyl]-piperidine-(R)-carboxylic acid methyl ester (0.18 g). This intermediate compound was treated according to the same procedure as Example 25 to obtain the purified title compound (0.16 g, Yield: 84%).

$^1$H NMR(CD$_3$OD, ppm) δ: 8.32, 7.95, 7.78–7.35(m, m, m, 11H), 4.71, 4.52(m, m, 1H), 3.97, 3.80(d, d, 1H), 3.73, 3.43(s, s, 3H), 3.10, 2.83, 2.39(m, m, m, 3H), 2.05(m, 1H), 1.65–1.00, 0.30(m, m, 6H)

Mass(FAB, m/e): 538(M$^+$+1)

EXAMPLE 49

Synthesis of 1-[3-(4-amidrazono-phenyl)-(S)-2-(naphthalene-2-sulfonylamino)-propionyl]-piperidine-(R)-2-carboxylic acid The compound prepared in Example 48 was treated according to the same procedure as Example 26 to obtain the purified title compound (0.03 g, Yield: 19%).

$^1$H NMR(CD$_3$OD, ppm) δ: 8.35, 8.00, 7.75–7.30(m, m, m, 11H), 4.50, 4.20(m, m, 1H), 3.89(m, 1H), 3.10, 2.82, 2.45(m, m, m, 3H), 2.10(m, 1H), 1.65–1.00, 0.25(m, m, 6H)

Mass(FAB, m/e): 524(M$^+$+1)

PREPARATION 13

Synthesis of (S)-4-[2-(butyloxycarbonyl-amino)-3-(4-methylsulfonyl-piperazinyl)-3-oxo-propyl]-benzonitrile (S)-3-(4-cyanophenyl)-2-(butyloxycarbonylamino) propionic acid (0.5 g, 1.7 mmole) was dissolved in dimethylformamide (DMF, 20 ml) and then cooled to 0° C. Then, 1-(3-dimethylaminopropyl)-3-ethylcarbodiimide hydrochloride (EDC, 0.5 g) and 1-hydroxybenzotriazole hydrate (HOBT, 0.3 g) were added to this solution and stirred until they are completely dissolved therein. To this reaction mixture were added 1-methanesulfonyl-piperazine (0.3 g) and N-methylmorpholine (0.2 ml), and then the temperature was slowly elevated to room temperature. The reaction solution was stirred for 3.5 hours. After the reaction is completed, the reaction solution was distilled under reduced pressure to remove the volatile substance and the remaining solution was diluted with ethyl acetate, washed successively with aqueous saturated sodium hydrogen carbonate solution, dilute hydrochloric acid and saturated saline, dried over anhydrous sodium sulfate, filtered and then concentrated. The residue was purified with column chromatography using ethyl acetate/hexane (6/4, by volume) as an eluent to obtain the purified title compound (0.7 g, Yield: 93%).

$^1$H NMR(CDCl$_3$, ppm) δ: 7.7–7.3(m, 4H), 5.3(m, 1H), 4.8(m, 1H), 3.9–3.55(m, 2H), 3.55–2.8(m, 8H), 2.7 (s, 3H), 1.5(s, 9H)

PREPARATION 14

Synthesis of (S)-naphthalene-2-sulfonic acid [1-(4-cyanobenzyl)-2-(4-methylsulfonyl-piperazinyl)-2-oxoethyl]amide The compound (0.7 g, 1.6 mmole) prepared in Preparation 13 was dissolved in dichloromethane (3 ml) and then cooled to −10° C., and trifluoroacetic acid (TFA, 3 ml) was added thereto. The reaction mixture was stirred for 5 minutes, slowly warmed to room temperature, stirred for 3 minutes and then distilled under reduced pressure to remove the volatile substance. The remaining solution was dried by means of a vaccum pump and then 20 ml of DMF was added thereto. The mixture was cooled to 0° C. and 2-naphthalenesulfonyl chloride (0.5 g) and diisopropylethylamine (0.9 ml) were added thereto. This mixture was stirred until the reactants are completely dissolved. The reaction mixture was slowly warmed to room temperature and stirred for 3 hours. Upon completion of the reaction, the reaction solution was distilled under reduced pressure to remove the volatile substance. The remaining solution was diluted with chloroform, washed successively with saturated sodium hydrogen carbonate, dilute hydrochloric acid and brine, dried over anhydrous sodium sulfate, filtered and concentrated. The residue was purified by column chromatography using chloroform/methanol (95/5, by volume) as an eluent to obtain the purified title compound (0.8 g, Yield: 95%).

$^1$H NMR(CDCl$_3$, ppm) δ: 8.3–7.2(m, 11H), 5.8(m, 1H), 4.5(m, 1H), 3.5–3.2(m, 2H), 2.45(s, 3H), 3.1–2.3(m, 8H)

EXAMPLE 50

Synthesis of (S)-naphthalene-2-sulfonic acid [1-(4-amidrazono)benzyl]-2-(4-methylsulfonyl-piperazinyl)-2-oxo-ethyl]-amide The compound (0.4 g, 0.76 mmole) prepared in Preparation 14 was dissolved in pyridine (5 ml) and the resulting solution was introduced into a branched flask, to which triethylamine (0.3 ml) was added. The reaction flask was equipped so that hydrogen sulfide (H$_2$S) gas can be slowly introduced through one branch of the flask and discharged through another branch. The reaction solution was saturated with hydrogen sulfide gas, while stirring for about 10 minutes, during which the colorless solution was changed into green color and then gradually into dark brown. The flask was closed with rubber stopper and allowed to stand for 3 days at room temperature. Then, the reaction solution was distilled under reduced pressure to remove the volatile substance and dried by means of a vaccum pump. To the obtained yellow solid were added acetone (10 ml) and iodomethane (0.5 ml) together and the mixture was heated under reflux for 30 minutes. This reaction mixture was distilled again under reduced pressure to remove the volatile substance and dried by means of a vaccum pump. The residue was dissolved in absolute methanol (5 ml) and then stirred. To this mixture was added portionwise 80% hydrazine hydrate (0.06 ml) over three times at an interval of 10 minutes. After the reaction is completed, the reaction solution was concentrated and then purified by HPLC to obtain the title compound (0.3 g, Yield: 65%).

$^1$H NMR(CD$_3$OD, ppm) δ: 8.4–7.4(m, 11H), 4.6(m, 1H), 3.5–3.2(m, 2H), 2.55(s, 3H), 3.1–2.2(m, 8H)

Mass(FAB, m/e): 559(M$^+$+1)

EXAMPLE 51

Synthesis of (S)-naphthalene-2-sulfonic acid [1-(4-amidrazono)benzyl-2-oxo-2-(4-ethoxycarbonyl-piperazinyl)-ethyl]amide The same procedure as Preparation 13, except that 1-piperazine ethyl carboxylate was used instead of 1-methanesulfonylpiperazine, was carried out and the resulting product was then treated according to the same procedure as Preparation 14 to obtain the intermediate (S)-naphthalene-2-sulfonic acid [1-(4-cyanobenzyl)-2-oxo-2-(4-ethoxycarbonyl-piperazinyl)-ethyl]amide (1 g, 1.9 mmole). This intermediate compound was treated according to the same procedure as Example 50 to obtain the purified title compound (0.6 g, Yield: 56%).

$^1$H NMR(CD$_3$OD, ppm) δ: 8.5–7.3(m, 11H), 4.55(m, 1H), 4.05(m, 2H), 3.2–2.4(m, 10H), 1.2(m, 3H)

Mass(FAB, m/e): 553(M$^+$+1)

EXAMPLE 52

Synthesis of (S)-naphthalene-2-sulfonic acid [1-(4-amidrazono)benzyl- 2-(4-formyl-piperazinyl-2-oxoethyl]amide The same procedure as Preparation 13, except that 1-piperazine ethylcarboxaldehyde was used instead of 1-methanesulfonylpiperazine, was carried out and the resulting product was then treated according to the same procedure as Preparation 14 to obtain the intermediate (S)-naphthalene-2-sulfonic acid [1-(4-cyanobenzyl)-2-(4-formyl-piperazinyl)-2-oxoethyl]amide (7 g, 1.6 mmole). This intermediate compound was treated according to the same procedure as Example 50 to obtain the purified title compound (0.5 g, Yield: 62%).

$^1$H NMR(CD$_3$OD, ppm) δ: 8.36–7.44(m, 11H), 4.60(m, 1H), 3.46–2.80(m, 9H), 2.55(m, 1H)

Mass(FAB, m/e): 509(M$^+$+1)

EXAMPLE 53

Synthesis of (S)-naphthalene-2-sulfonic acid [1-(4-amidrazono)benzyl-2-(4-ethyl-piperazinyl)-2-oxoethyl]amide The same procedure as Preparation 13, except that 1-ethylpiperazine was used instead of 1-methanesulfonylpiperazine, was carried out and the resulting product was then treated according to the same procedure as Preparation 14 to obtain the intermediate (S)-naphthalene-2-sulfonic acid [1-(4-cyanobenzyl)-2-(4-ethyl-piperazinyl)-oxoethyl]amide (0.3 g, 0.6 mmole). This intermediate compound was treated according to the same procedure as Example 50 to obtain the purified title compound (0.2 g, Yield: 56%).

$^1$H NMR(CD$_3$OD, ppm) δ: 8.5–7.3(m, 11H), 4.6(m, 1H), 3.5–2.7(m, 10H), 2.2(s, 2H), 1.4–1.2(m, 3H)

Mass(FAB, m/e): 509(M$^+$+1)

EXAMPLE 54

Synthesis of (S)-naphthalene-2-sulfonic acid [1-(4-amidrazono)benzyl-2-oxo-2-(4-phenylpiperazinyl)-ethyl]amide The same procedure as Preparation 13, except that 1-phenylpiperazine was used instead of 1-methanesulfonylpiperazine, was carried out and the resulting product was then treated according to the same procedure as Preparation 14 to obtain the intermediate (S)-naphthalene-2-sulfonic acid [1-(4-cyanobenzyl)-2-oxo-2-(4-phenyl-piperazinyl)-ethyl]-amide (0.5 g, 0.97 mmole). This intermediate compound was treated according to the same procedure as Example 50 to obtain the purified title compound (0.3 g, Yield: 57%).

$^1$H NMR(CD$_3$OD, ppm) δ: 8.35–7.54(m, 11H), 7.20(m, 2H), 6.86(m, 1H), 6.67(m, 2H), 4.56(m, 1H), 3.45(m, 1H), 3.25–2.92(m, 5H), 3.72(m, 2H), 2.42(m, 1H), 2.05(m, 1H)

Mass(FAB, m/e): 557(M$^+$+1)

EXAMPLE 55

Synthesis of (S)-naphthalene-2-sulfonic acid [1-(4-amidrazono)benzyl-2-oxo-2-[4-(3-trifluoromethyl-phenyl)-piperazinyl]-ethyl]-amide The same procedure as Preparation 13, except that 1-(α,α,α-trifluoro-m-tolyl)piperazine was used instead of 1-methanesulfonylpiperazine, was carried out and the resulting product was then treated according to the same procedure as Preparation 14 to obtain the intermediate (S)-naphthalene-2-sulfonic acid [1-(4-cyanobenzyl)-2-oxo-2-[4-(3-trifluoromethyl-phenyl)-piperazinyl]-ethyl]amide (0.5 g, 0.8 mmole). This intermediate compound was treated according to the same procedure as Example 50 to obtain the purified title compound (0.3 g, Yield: 55%).

$^1$H NMR(CD$_3$OD, ppm) δ: 8.35–6.7(m, 15H), 3.47(m, 1H), 3.3–3.0(m, 5H), 3.76(m, 2H), 2.45(m, 1H), 2.03(m, 1H)

Mass(FAB, m/e): 625(M$^+$+1)

EXAMPLE 56

Synthesis of (S)-naphthalene-2-sulfonic acid [2-(4-acetyl-piperazinyl)-1-(4-amidrazono)benzyl-2-oxoethyl]amide The same procedure as Preparation 13, except that 1-acetylpiperazine was used instead of 1-methanesulfonylpiperazine, was carried out and the resulting product was then treated according to the same procedure as Preparation 14 to obtain the intermediate (S)-naphthalene-2-sulfonic acid [2-(4-acetyl-piperazinyl)-1-(4-cyanobenzyl)-2-oxo-ethyl]-amide (.1.25 g, 2.55 mmole). This intermediate compound was treated according to the same procedure as Example 50 to obtain the purified title compound (0.7 g, Yield: 53%).

$^1$H NMR(CD$_3$OD, ppm) δ: 8.4–7.4(m, 11H), 4.5(m, 1H), 3.5–3.2(m, 2H), 3.1–2.2(m, 8H), 2.0(s, 3H)

Mass(FAB, m/e): 523(M$^+$+1)

EXAMPLE 57

Synthesis of (S)-naphthalene-2-sulfonic acid [1-(4-amidrazono)benzyl-2-oxo-2-[4-(2-hydroxyethyl)-piperazinyl]-ethyl]amide The same procedure as Preparation 13, except that 1-piperazine ethane is used instead of 1-methanesulfonylpiperazine, was carried out and the resulting product was then treated according to the same procedure as Preparation 14 to obtain the intermediate (S)-naphthalene-2-sulfonic acid [1-(4-cyanobenzyl)-2-oxo-2-[4-(2-hydroxyethyl)-piperazinyl]ethyl]amide (0.07 g, 0.14 mmole). This intermediate compound was treated according to the same procedure as Example 50 to obtain the purified title compound (0.05 g, Yield: 68.5%).

$^1$H NMR(CD$_3$OD, ppm) δ: 8.35–7.30(m, 11H), 4.60(m, 1H), 3.96–3.7(m, 4H), 3.70–2.80(m, 10H)

Mass(FAB, m/e): 525(M$^+$+1)

EXAMPLE 58

Synthesis of (S)-naphthalene-2-sulfonic acid [1-(4-amidrazono)benzyl-2-oxo-2-[4-(2-ethoxyphenyl)-piperazinyl]-ethyl]amide The same procedure as Preparation 13, except that 1-(2-ethoxyphenyl)piperazine was used instead of 1-methanesulfonylpiperazine, was carried out and the resulting product was then treated according to the same procedure as Preparation 14 to obtain the intermediate (S)-naphthalene-2-sulfonic acid [1-(4-cyanobenzyl)-2-oxo-2-[4-(2-ethoxyphenyl)-piperazinyl]ethyl]amide (0.4 g, 0.7 mmole). This intermediate compound was treated according to the same procedure as Example 50 to obtain the purified title compound (0.26 g, Yield: 62%).

$^1$H NMR(CD$_3$OD, ppm) δ: 8.36–6.54(m, 15H), 4.6(m, 1H), 4.01(m, 2H), 3.48(m, 1H), 3.28–3.08(m, 5H), 2.69(m, 2H), 2.38(m, 1H), 2.08(m, 1H), 1.35(m, 3H)

Mass(FAB, m/e): 601(M$^+$+1)

Test 1
Inhibitory Activity for Thrombin

The ability of the compound according to the present invention to inhibit the thrombin activity was determined as described in the following.

1160 μl of 0.1M tris buffered solution (pH 7.8) containing 150 mM NaCl and 0.1% PEG 8000 (polyethylene glycol, molecular weight about 8,000) was added to a 1.5 ml cuvette. Chromozym TH was dissolved in dimethylsulfoxide (DMSO) in the concentration of 10 mM and the resulting solution was diluted with the said tris buffered solution to the concentration of 0.1 mM, which was then used as the substrate solution. 225 μl of 0.1 mM substrate solution thus prepared was added to the cuvette. The inhibitor solution was prepared by dissolving the thrombin inhibitor compound according to the present invention in dimethylsulfoxide in the concentration of 10 mg/ml and then diluting the resulting solution with the said tris buffered solution to the concentration of 0.1 mg/ml, 0.01 mg/ml, 0.001 mg/ml and 0.0001 mg/ml. The resulting inhibitor solution was taken in an amount corresponding to 0 to 10 μg as the inhibitor and then diluted with tris buffered solution to make the total volume of 100 μl which was added to the cuvette.

15 μl of bovine thrombin solution dissolved in above tris buffered solution in the concentration of 0.1 mg/ml was added to the cuvette to initiate the enzyme hydrolysis reaction. The amount of para-nitroaniline produced for 2 minutes from the moment the enzyme is added was monitored by measuring the absorbance at 381 nm. The continuous spectrum of absorbance to reaction time was depicted. The same experiments were conducted for various concentration of the inhibitor to obtain the continuous spectrum.

In each spectrum, the initial velocity Vi was obtained from the slope within initial 30 seconds of the reaction time and then a graph for the reciprocal value of initial velocity (1/Vi) to the inhibitor concentration was depicted. From the graph, the primary equation satisfying the points depicted thereon was obtained and then the value Ki was calculated from the x intercept of the primary equation using the enzyme reaction equation. The value Km used for this calculation was 8.3 μM which was obtained by changing the substrate concentration at the constant enzyme concentration.

The velocity constant Ks was obtained using the same solution in the same concentration as in determination of the value Ki but using the following experimental procedure.

Specifically, 1160 μl of the buffered solution was added to a 1.5 ml cuvette, and 15 μl of bovine thrombin solution having 0.1 mg/ml concentration and 100 μl of the inhibitor solution were added thereto. The mixture was allowed to stand at room temperature for 15 minutes. Then, while adding 225 μl of 0.1 mM substrate solution, the change of absorbance in the course of time was monitored for 2 minutes. From the obtained continuous spectrum, the slope at the straight portion was determined and represented as the value Vs. The same experiment was conducted for various concentration of the inhibitor to obtain the value Vs at each concentration of the ihibitor from which the graph for 1/Vs against the inhibitor concentration was depicted. From the graph, the primary equation satisfying the points depicted thereon was obtained and then the value Ks was calculated from the x intercept of the primary equation using the enzyme reaction equation.

Separately, the inhibitory activity of the compound according to the present invention for trypsin was determined in the same manner as in determination of the inhibitory activity for thrombin as described above.

As the substrate 20 μM solution of N-benzoyl-Val-Gly-Arg-p-nitroanilide hydrochloride was used, and the inhibitor was used in various concentrations within the range of 0 to 120 μg. In addition, trypin was dissolved in 0.1N HCl, adjusted to the concentration of 45 μg/ml with the said tris buffered solution just before the experiment, and then used in an amount of 40 μl. As in the experiment for thrombin, a total volume of the reaction solution was 1.5 ml and the remaining procedure was conducted in the same manner. The value Km used in calculation of the value Ki was determined according to the same method as in the experiment for thrombin above and was 20.2 μM.

The inhibitory activity of the compound according to the present invention for the activity of each enzyme as determined according to the above method was represented by the values Ki and Ks and the selectivity for thrombin was represented by trypsin inhibitory activity/thrombin inhibitory activity. The result thus obtained is described in the following Table 1.

TABLE 1

Inhibitory activity of the compound according to the present invention for thrombin and trypsin

| Comp. No. (Ex.) | Inhibitory activity for thrombin | | Inhibitory activity for trypsin | | Selectivity (trypsin/ thrombin) |
|---|---|---|---|---|---|
| 1 | Ki = 0.0038 | μM | Ki = 3.19 | μM | 2900 |
|   | Ks = 0.0011 | μM |   |   |   |
| 2 | Ki = 0.041 | μM |   |   |   |
| 3 | Ki = 0.093 | μM |   |   |   |
| 4 | Ki = 0.345 | μM |   |   |   |
| 5 | Ki = 0.231 | μM |   |   |   |
| 6 | Ki = 0.00435 | μM |   |   |   |
| 7 | Ki = 0.0138 | μM | Ki = 363 | μM | 26304 |
| 9 | Ki = 0.227 | μM |   |   |   |
| 10 | Ki = 0.367 | μM |   |   |   |
| 13 | Ki = 0.216 | μM |   |   |   |
| 15 | Ki = 0.152 | μM |   |   |   |
| 16 | Ki = 0.247 | μM |   |   |   |
| 17 | Ki = 0.016 | μM |   |   |   |
| 18 | Ki = 0.011 | μM | Ki = 3.98 | μM | 2000 |
|   | Ks = 0.002 | μM |   |   |   |
| 19 | Ki = 0.0053 | μM | Ki = 5.25 | μM | 990 |
| 20 | Ki = 0.0217 | μM | Ki = 2.3 | μM | 106 |
| 21 | Ki = 0.025 | μM | Ki > 100 | μM | >10000 |
|   | KS = 0.009 | μM |   |   |   |
| 22 | Ki = 0.017 | μM |   |   |   |
| 23 | Ki = 2.59 | μM | Ki = 21.7 | μM | 8 |
| 24 | Ki = 20.1 | μM |   |   |   |
| 25 | Ki = 0.259 | μM |   |   |   |
| 27 | Ki = 0.065 | μM |   |   |   |
| 29 | Ki = 0.089 | μM |   |   |   |
| 31 | Ki = 0.165 | μM |   |   |   |
| 33 | Ki = 0.035 | μM |   |   |   |
| 35 | Ki = 0.612 | μM |   |   |   |
| 39 | Ki = 0.165 | μM |   |   |   |
| 45 | Ki = 0.346 | μM |   |   |   |
| 46 | Ki = 0.880 | μM |   |   |   |
| 47 | Ki = 0.665 | μM |   |   |   |
| 48 | Ki = 0.013 | μM |   |   |   |
| 49 | Ki = 0.406 | μM |   |   |   |
| 50 | Ki = 0.011 | μM | Ki = 5.79 | μM | 965 |
|   | Ks = 0.006 | μM |   |   |   |
| 51 | Ki = 3.3 | μM |   |   |   |
| 52 | Ki = 0.05 | μM |   |   |   |
| 53 | Ki = 0.530 | μM |   |   |   |
| 54 | Ki = 5.380 | μM |   |   |   |
| 55 | Ki = 10.000 | μM |   |   |   |
| 56 | Ki = 0.280 | μM |   |   |   |
| 57 | Ki = 0.068 | μM |   |   |   |
| 58 | Ki = 9.130 | μM |   |   |   |

Test 2

Pharmacokinetic Test

Test Method

Male rats and dogs were fasted for 24 hours and used as the experimental animals. 1% solution (10 mg/ml) of the compound of Example 1 was prepared using physiological saline and then administered to the experimental animals via intravenous and oral route. Bloods were collected from the animals at given time intervals and then immediately mixed with methanol and zinc sulfate. Finally, the upper layer of the mixture was quantitatively analyzed at ultraviolet wavelength of 231 nm to measure the drug concentration in blood by HPLC.

Test Result

The drug concentration and the pharmacokinetic parameters of the compound of Example 1 following intravenous and oral administration are listed in the following Tables 2 to 7. When the compound of Example 1 was intravenously injected, it was rapidly distributed and then slowly disappeared in both rats and dogs, whereas the elimination half-life of the compound in dogs was twice longer or more than that in rats. Furthermore, the elimination half-life of the compound of Example 1 in dogs was twice longer or more than that of commercially available argatroban (40 minutes) in human being (see, Osamu et al., Pharmacology and Therapy, vol. 14, suppl. 5, 1986). Meanwhile, it could also be identified that the bioavailability of the compound of Example 1 was 15% in rats and 61% in dogs, it was administered via oral route. However, it has been reported that argatroban was not absorbed in animals and human being when it was administered via oral route.

From the above results, the compound of Example 1 showed the better pharmacokinetic characteristics than argatroban in terms of oral absorption and elimination half-life.

TABLE 2

Blood concentration of the compound of Example 1 following intravenous injection of 10 mg/kg in rats

| Time | Blood concentration (ng/ml) | | | Average (+error) |
|---|---|---|---|---|
| (min.) | Rat-1 | Rat-2 | Rat-3 | (ng/ml) |
| 1 | 31503 | 23000 | 31964 | 28822 (2914) |
| 3 | 8105 | 6773 | 7884 | 7587 (412) |
| 5 | 3976 | 3066 | 4223 | 3755 (352) |
| 10 | 1907 | 1828 | 1928 | 1888 (31) |
| 20 | 918 | 898 | 883 | 900 (10) |
| 30 | 631 | 600 | 591 | 607 (12) |
| 45 | 355 | 408 | 398 | 387 (16) |
| 60 | 270 | 242 | 289 | 267 (14) |
| 90 | 168 | 166 | 184 | 173 (6) |
| 120 | 76 | 97 | 119 | 97 (12) |
| 180 | 87 | 73 | 78 | 79 (4) |

TABLE 3

Blood concentration of compound of Example 1 following oral administration of 15 mg/kg in rats

| Time | Blood concentration (ng/ml) | | | Average (+error) |
|---|---|---|---|---|
| (min.) | Rat-1 | Rat-2 | Rat-3 | (ng/ml) |
| 5 | 1610 | 822 | 570 | 1001 (313) |
| 10 | 1478 | 686 | 384 | 850 (326) |
| 20 | 569 | 166 | 97 | 255 (147) |
| 30 | 232 | 82 | 113 | 143 (46) |
| 45 | 145 | 107 | 112 | 121 (12) |
| 60 | 143 | 123 | 110 | 125 (9) |
| 90 | 66 | 186 | 119 | 124 (35) |
| 120 | 34 | | 71 | 53 (19) |
| 180 | 24 | 238 | 64 | 109 (66) |

TABLE 4

Pharmacokinetic parameters of the compound of Example 1 in rats

| Parameter | Average + (error) |
|---|---|
| Elimination Half-life (min.) | 47 (1) |
| Bioavailability (%) | 15 (2) |

TABLE 5

Blood drug concentration of the compound of Example 1 following intravenous injection of 10 mg/kg in dogs

| Time | Blood concentration (ng/ml) | | Average (+error) |
|---|---|---|---|
| (min.) | Dog-1 | Dog-2 | (ng/ml) |
| 2 | 29121 | 36648 | 32885 (3764) |
| 5 | 9082 | 5226 | 7155 (1927) |
| 10 | 5935 | 3282 | 4608 (1327) |
| 20 | 3610 | 1801 | 2706 (904) |
| 30 | 2433 | 1335 | 1884 (549) |
| 45 | 1937 | 859 | 1398 (539) |
| 60 | 1471 | 690 | 1081 (391) |
| 90 | 1269 | 501 | 885 (384) |
| 120 | 1090 | 377 | 733 (357) |
| 240 | 544 | 129 | 337 (207) |
| 300 | 315 | 107 | 211 (104) |
| 360 | 317 | 92 | 204 (112) |

TABLE 6

Blood concentration of the compound of Example 1. following oral administration of 10 mg/kg in dogs

| Time | Blood concentration (ng/ml) | | Average (+error) |
|---|---|---|---|
| (min.) | Dog-1 | Dog-2 | (ng/ml) |
| 10 | 1389 | 15 | 702 (687) |
| 20 | 2076 | 17 | 1047 (1029) |
| 30 | 1942 | 105 | 1023 (918) |
| 45 | 1891 | 558 | 1225 (667) |
| 60 | 2215 | 1312 | 1763 (451) |
| 90 | 1273 | 935 | 1104 (169) |
| 120 | 774 | 730 | 752 (22) |
| 180 | 663 | 616 | 640 (24) |
| 240 | 812 | 318 | 565 (247) |
| 300 | 51 | 222 | 136 (66) |
| 360 | 118 | 153 | 135 (18) |

TABLE 7

Pharmacokinetic parameters of the compound of Example 1 in dogs

| Parameter | Average + (error) |
|---|---|
| Elimination Half-life (min.) | 98 (15) |
| Bioavailability (%) | 61 (15) |

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A compound represented by the following formula (I):

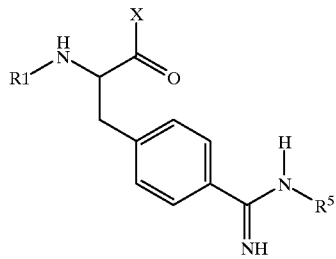

or its pharmaceutically acceptable salt, hydrate, solvate and isomer, in which $R^1$ represents sulfonyl substituted with substituted or unsubstituted aryl, x represents a group of formula

$R^2$ and $R^3$ together with nitrogen atom to which they are attached form a piperidine group substituted with carboxyl or alkoxycarbonyl, and $R^6$ represents methyl or amino.

2. The compound of formula (I) as defined in claim 1, in which $R^1$ represents sulfonyl substituted with naphthyl or phenyl which can be substituted or unsubstituted with one to four substituents selected from the group consisting of lower alkyl, lower alkoxy and dialkylamino, X represents a group of formula

$R^2$ and $R^3$ together with nitrogen atom to which they are attached form a piperidine group substituted with carboxyl or methoxycarbonyl.

3. The compound of formula (I) as defined in claim 2, wherein the compound is selected from the group consisting of:

1-[3-(4-amidrazonophenyl)-(S)-2-(naphthalene-2-sulfonylamino)-propionyl]-piperidine-(R)-2-carboxylic acid methyl ester, 1-[3-(4-amidrazonophenyl)-(S)-2-(naphthalene-2-sulfonylamino)-propionyl]-piperidine-(R)-2-carboxylic acid.

4. A pharmaceutical composition for thrombin inhibition, which comprises the compound as defined in any one of claims 1 to 3 as an active ingredient together with a pharmaceutically acceptable carrier.

5. The pharmaceutical composition as defined in claim 4, wherein the composition is formulated into an oral preparation.

* * * * *